(12) United States Patent
Poncz et al.

(10) Patent No.: US 9,259,443 B2
(45) Date of Patent: Feb. 16, 2016

(54) COMPOSITIONS AND METHODS FOR THE GENERATION OF PLATELETS AND METHODS OF USE THEREOF

(75) Inventors: Mortimer Poncz, Philadelphia, PA (US); Mitchell Weiss, Wynnewood, PA (US); Paul Gadue, Philadelphia, PA (US); Deborah French, Newark, DE (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 13/881,587

(22) PCT Filed: Oct. 25, 2011

(86) PCT No.: PCT/US2011/057716
§ 371 (c)(1),
(2), (4) Date: Dec. 16, 2013

(87) PCT Pub. No.: WO2012/061146
PCT Pub. Date: May 10, 2012

(65) Prior Publication Data
US 2014/0086883 A1    Mar. 27, 2014

Related U.S. Application Data

(60) Provisional application No. 61/406,514, filed on Oct. 25, 2010.

(51) Int. Cl.
| | | |
|---|---|---|
| *C12N 5/00* | (2006.01) | |
| *C12N 5/02* | (2006.01) | |
| *C12N 5/074* | (2010.01) | |
| *C12N 5/07* | (2010.01) | |
| *A61K 35/28* | (2015.01) | |
| *C12N 5/078* | (2010.01) | |
| *A61K 35/19* | (2015.01) | |

(52) U.S. Cl.
CPC ............. *A61K 35/28* (2013.01); *A61K 35/19* (2013.01); *C12N 5/0644* (2013.01); *C12N 2501/115* (2013.01); *C12N 2501/125* (2013.01); *C12N 2501/145* (2013.01); *C12N 2501/155* (2013.01); *C12N 2501/16* (2013.01); *C12N 2501/165* (2013.01); *C12N 2501/2303* (2013.01); *C12N 2501/2306* (2013.01); *C12N 2501/2311* (2013.01); *C12N 2501/60* (2013.01); *C12N 2506/02* (2013.01)

(58) Field of Classification Search
None
See application file for complete search history.

(56) References Cited

U.S. PATENT DOCUMENTS

| | | |
|---|---|---|
| 5,571,686 A | 11/1996 | Rosenberg et al. |
| 5,753,506 A | 5/1998 | Johe |
| 5,811,297 A | 9/1998 | Gopal |
| 5,817,662 A | 10/1998 | Klein et al. |
| 5,824,297 A | 10/1998 | Iwata et al. |
| 5,871,724 A | 2/1999 | Iwata et al. |
| 5,889,011 A | 3/1999 | Klein et al. |
| 5,997,860 A | 12/1999 | Bauer et al. |
| 6,040,180 A | 3/2000 | Johe |
| 6,066,778 A | 5/2000 | Ginsburg et al. |
| 6,248,587 B1 | 6/2001 | Rodgers et al. |
| 6,291,210 B1 | 9/2001 | Sakano et al. |
| 6,337,387 B1 | 1/2002 | Sakano et al. |
| 6,465,620 B1 | 10/2002 | Boyle et al. |
| 6,569,662 B1 | 5/2003 | Tang et al. |
| 6,586,390 B1 | 7/2003 | Haley et al. |
| 6,602,705 B1 | 8/2003 | Barnett et al. |
| 6,673,904 B2 | 1/2004 | Nishikawa et al. |
| 6,846,647 B1 | 1/2005 | Honjo et al. |
| 2002/0146823 A1 | 10/2002 | Rodgers et al. |
| 2003/0091547 A1 | 5/2003 | Edelberg et al. |
| 2003/0235959 A1 | 12/2003 | Hariri et al. |
| 2004/0006003 A1 | 1/2004 | Rodgers et al. |
| 2004/0028660 A1 | 2/2004 | Hariri |
| 2004/0192599 A1 | 9/2004 | Schuh |
| 2005/0086710 A1 | 4/2005 | Peluso et al. |
| 2005/0118715 A1 | 6/2005 | Hariri |
| 2005/0266557 A1 | 12/2005 | Proulx |
| 2006/0099198 A1 | 5/2006 | Thomson |
| 2006/0134783 A1 | 6/2006 | Fong et al. |
| 2007/0077654 A1 | 4/2007 | Daigh |
| 2008/0275049 A1 | 11/2008 | Polikandriotis et al. |
| 2009/0148425 A1 | 6/2009 | Ohmori et al. |

FOREIGN PATENT DOCUMENTS

| | | |
|---|---|---|
| JP | 11-180877 | 7/1999 |
| WO | 2008/151386 | 12/2008 |

OTHER PUBLICATIONS

Gropp et al., Cloning and Stem Cells 2007, 9(3)339-345.*
Takayama, N., et al. "In vitro generation of megakaryocytes and platelets from human embryonic stem cells and induced pluripotent stem cells." Methods Mol Biol. 2012;788:205-17.
Chen, T.W., et al. "Characterization and transplantation of induced megakaryocytes from hematopoietic stem cells for rapid platelet recovery by a two-step serum-free procedure." Exp Hematol. Nov. 2009;37(11):1330-1339.e5. Epub Aug. 5, 2009.
Weiss, M.J., et al. "Novel insights into erythroid development revealed through in vitro differentiation of GATA-1 embryonic stem cells." Genes Dev. May 15, 1994;8(10):1184-97.
Fuentes, R., et al. "Infusion of mature megakaryocytes into mice yields functional platelets." J Clin Invest. Nov. 2010;120(1)):3917-3922.
Stachura, et al. Early block to erythromegakaryotic development conferred by loss of transcriptional factor GATA-1 Blood. 2006;107:87-97.
Shivdassani, et al. "A lineage-selective knockout establishes the critical role of transcription factor GATA-1 in megakaryocyte growth and platelet development." EMBO J. 1997;16:3965-3973.

* cited by examiner

*Primary Examiner* — Doug Schultz
(74) *Attorney, Agent, or Firm* — Robert C. Netter, Jr.; Dann, Dorfman, Herrell & Skillman

(57) ABSTRACT

Compositions and methods for generating platelets and methods of use thereof are disclosed.

9 Claims, 19 Drawing Sheets

COMPOSITIONS AND METHODS FOR THE GENERATION OF PLATELETS AND METHODS OF USE THEREOF

This application is a §371 application of PCT/US2011/057716, filed Oct. 25, 2011, which claims priority under 35 U.S.C. §119(e) to U.S. Provisional Patent Application No. 61/406,154, filed on Oct. 25, 2010. The foregoing applications are incorporated by reference herein.

This invention was made with government support under Grant No. U01HL99656 awarded by the National Heart, Lung and Blood Institute. The Government has certain rights in this invention.

FIELD OF THE INVENTION

The present invention relates to the field of hematology and related diseases and disorders. More specifically, the invention provides compositions and methods for the generation of platelets from ex vivo grown megakaryocytes.

BACKGROUND OF THE INVENTION

Several publications and patent documents are cited throughout the specification in order to describe the state of the art to which this invention pertains. Full citations of these references can be found throughout the specification. Each of these citations is incorporated herein by reference as though set forth in full.

Platelets are critical for hemostasis and are anucleate cellular fragments derived from megakaryocytes (Kaushansky, K. (2008) Blood 111:981-6). Platelets also have important roles in angiogenesis and inflammation (Browder et al. (2000) J. Biol. Chem., 275:1521-4; May et al. (2008) Arterioscler. Thromb. Vasc. Biol., s5-10). Transfusions of platelets are used in diverse clinical settings, including individuals with decreased platelet production, for example, secondary to chemotherapy-induced thrombocytopenia (CIT) (Benjamin et al. (2002) Crit. Rev. Oncol. Hematol., 42:163-71), and those with increased platelet destruction, for example, in patients with disseminated intravascular coagulopathies (Dempfle, C. E. (2004) Thromb. Haemost., 91:213-24). In 2001 in the USA, platelet transfusions totaled 10,196,000 units, an increase of 12.6% from 1999 (Sullivan et al. (2007) Transfusion 47:385-394). The use of single-donor apheresis platelets increased at the same time by 26% to 7,582,000 platelet concentrate units.

While the number of platelet donors is increasing, there is still a significant donor shortage due to the growing population of patients with serious illnesses associated with thrombocytopenia and hemorrhage (Sullivan et al. (2007) Transfusion, 47:385-394). At present, platelet transfusions are limited by their short storage half-life, apheresis requiring a donor to undergo a 2-hour procedure, and units varying significantly both qualitatively and quantitatively (Kaufman, R. M. (2006) Hematology Am. Soc. Hematol. Educ. Progr., 492-6; Heddle et al. (2008) Transfusion 48:1447-589; Garner et al. (2008) Transfusion 48:673-80). Because platelets have to be stored at room temperature, these units have the highest incidence of bacterial contamination (Eder et al. (2007) Transfusion 47:1134-42). Even with leuko-reduction to remove contaminating white cells, there is still a high incidence of inhibitors developing in multiply transfused patients (Seftel et al. (2004) Blood 103:333-9). Thus, the use of donor-derived platelets raises the following concerns: variability of quality and quantity, risk of infectious transmission, short lifespan of stored platelets, bacterial contamination during storage, and development of alloantibodies in multi-transfused patients. These problems highlight a need for new strategies to generate platelets for infusion therapy.

Thrombopoiesis, the process by which circulating platelets arise from megakaryocytes remains incompletely understood. In vitro studies suggest that platelets form nodes at tips of proplatelet strands (Italiano et al. (1999) J. Cell. Biol., 147:1299-1312). However, direct visualization of live calvaria marrow using multiphoton intravital microscopy suggests that megakaryocytes release large cytoplasmic fragments into the vasculature (Junt et al. (2007) Science 317:1767-1770), which must then undergo reorganization into platelets. Studies based on morphologic analysis and quantification of megakaryocyte-like polyploid nuclei in the pulmonary venous system suggested that megakaryocytes release platelets in the lungs (Zucker-Franklin et al. (2000) Am. J. Pathol., 157:69-74). Derivation of platelets from megakaryocytes in culture has been reported (Choi et al. (1995) Blood 85:402-413) but has been difficult to quantitatively upscale. Present day efforts to develop platelets ex vivo have met with very limited and not clinically relevant results. To date, the best published result from infused in vitro produced platelets used irradiated mice with low platelet counts ($\sim 10^4/\mu l$) (Nishikii et al. (2008) J. Exp. Med., 205:1917-1927). Peak percent donor platelet counts were still only 1%-2%.

SUMMARY OF THE INVENTION

In accordance one aspect of the instant invention, methods of treating, inhibiting, and/or preventing thrombocytopenia in a subject are provided. The methods comprise delivering megakaryocytes and/or platelets to a subject in need thereof. In certain embodiments, the method comprises: a) decreasing the expression of GATA-1 in stem cells (e.g., pluripotent stem cells such as human embryonic stem cells, hematopoietic stem cells, or induced pluripotent stem (iPS) cells), thereby generating GATA-1 knockout or knockdown stem cells; b) culturing the GATA-1 knockout or knockdown stem cells, optionally with stromal cells, in the presence of thrombopoietin, thereby generating a self-replicating, megakaryocyte-erythroid progenitor (MEP) cell termed GATA-1 megakaryocyte-erythroid (G1ME) cells; c) expressing GATA-1 in the G1ME cells and having the cells undergo final differentiation into erythrocytes and megakaryocytes; d) isolating megakaryocytes from the cells of step c) (e.g., isolating large cells, optionally via a step gradient); and e) administering the isolated megakaryocytes to the subject. These megakaryocytes then release a clinically relevant number of circulating function platelets, thereby treating the thrombocytopenia. In a particular embodiment, the platelets are generated in vitro and then administered to the subject, thereby treating the thrombocytopenia. In certain embodiments, the method comprises: a) decreasing the expression of GATA-1 in hematopoietic cells derived from stem cells (e.g., human embryonic stem (ES) cells or induced pluripotent stem (iPS) cells), thereby generating GATA-1 knockout or knockdown stem cells; b) culturing the GATA-1 knockout or knockdown stem cells, optionally with stromal cells, in the presence of thrombopoietin, thereby generating G1ME cells; c) expressing GATA-1 in the G1ME cells; d) isolating megakaryocytes from the cells of step c); and e) administering the isolated mature megakaryocytes to the subject. These megakaryocytes then release a clinically relevant number of circulating function platelets, thereby treating the thrombocytopenia. In a particular embodiment, the MEP-like, G1ME cells described above are immortal and TPO-dependent. Compositions comprising the pre-megakaryocyte cell line and a carrier are also encompassed by the instant invention as well as methods of generating the same. In certain embodiments, the megakaryocytes are obtained from adult bone marrow or fetal liver. For example, the bone marrow or fetal liver cells are cultured with TPO, optionally with stromal cells, and large mature megakaryocytes are isolated. In certain embodiments, the megakaryocytes are derived from stem cells via an erythroid body. The methods may further comprise the delivery of a nucleic acid molecule encoding a protein of interest to the cells of the above methods, particularly prior to administration to the subject.

In accordance with another aspect of the instant invention, methods of delivering a protein of interest (e.g., a therapeutic protein) to a subject are provided. The method comprises the steps set forth above, wherein the cells express the protein of interest. In certain embodiments beginning with ES, iPS or hematopoietic progenitor cells, the cells' nuclei will have been targeted to express (ectopically) a protein of interest, particularly one not normally seen within megakaryocytes or platelets, to use the platelets as a therapeutic delivery vehicle to site of vascular injury to modulation coagulation/thrombosis, fibrinolysis, angiogenesis or inflammation. These proteins will be stored in the granules of the platelet to be delivered after platelet activation in a concentrated fashion at the site of vascular injury. Methods of treating, inhibiting, and/or preventing a disease or disorder in a subject are also provided, wherein the protein of interest is therapeutic for the disease or disorder to be treated. The therapeutic methods may be combined with one or more known therapeutic methods for the disease or disorder to be treated.

In certain embodiments involving iPS cells, the derived megakaryocytes may allow individualized care (autologous use) for a patient resistant to conventional platelet transfusion secondary to alloimmunization after repeated platelet exposure. iPS cells are pluripotent stem cell artificially derived from a non-pluripotent cell, typically an adult somatic cell (see, e.g., Takahashi et al. (2006) Cell 126:663-76; Takahashi et al. (2007) Cell 131:861-72, Yu et al. (2007) Science 318:1917; US Patent Application Publication Nos. 2011/0200568 and 2011/0189137). In certain embodiments involving iPS cells, the patients will have an inherited platelet disorder, and their derived iPS cells will have undergone genetic modification that corrects the platelet disorder and leads to infused megakaryocytes releasing functionally normal platelets. As with the other megakaryocytes described hereinbelow, iPS cell derived megakaryocytes were determined to give rise to platelets in NSG mice (up to 2% of circulating platelets was observed).

BRIEF DESCRIPTION OF THE DRAWINGS

FIG. 2 shows the characterization of the megakaryocytes infused and the resulting platelets generated in vivo.

FIG. 3 shows that the platelets are functional and cane be incorporated into arterial clots after laser injury.

FIG. 4 shows organ distribution studies of infused megakaryocytes and where they shed platelets.

FIG. 7 shows that infused human ex vivo-grown megakaryocytes also shed platelets after infusion into a mouse.

DETAILED DESCRIPTION OF THE INVENTION

Figure 1:
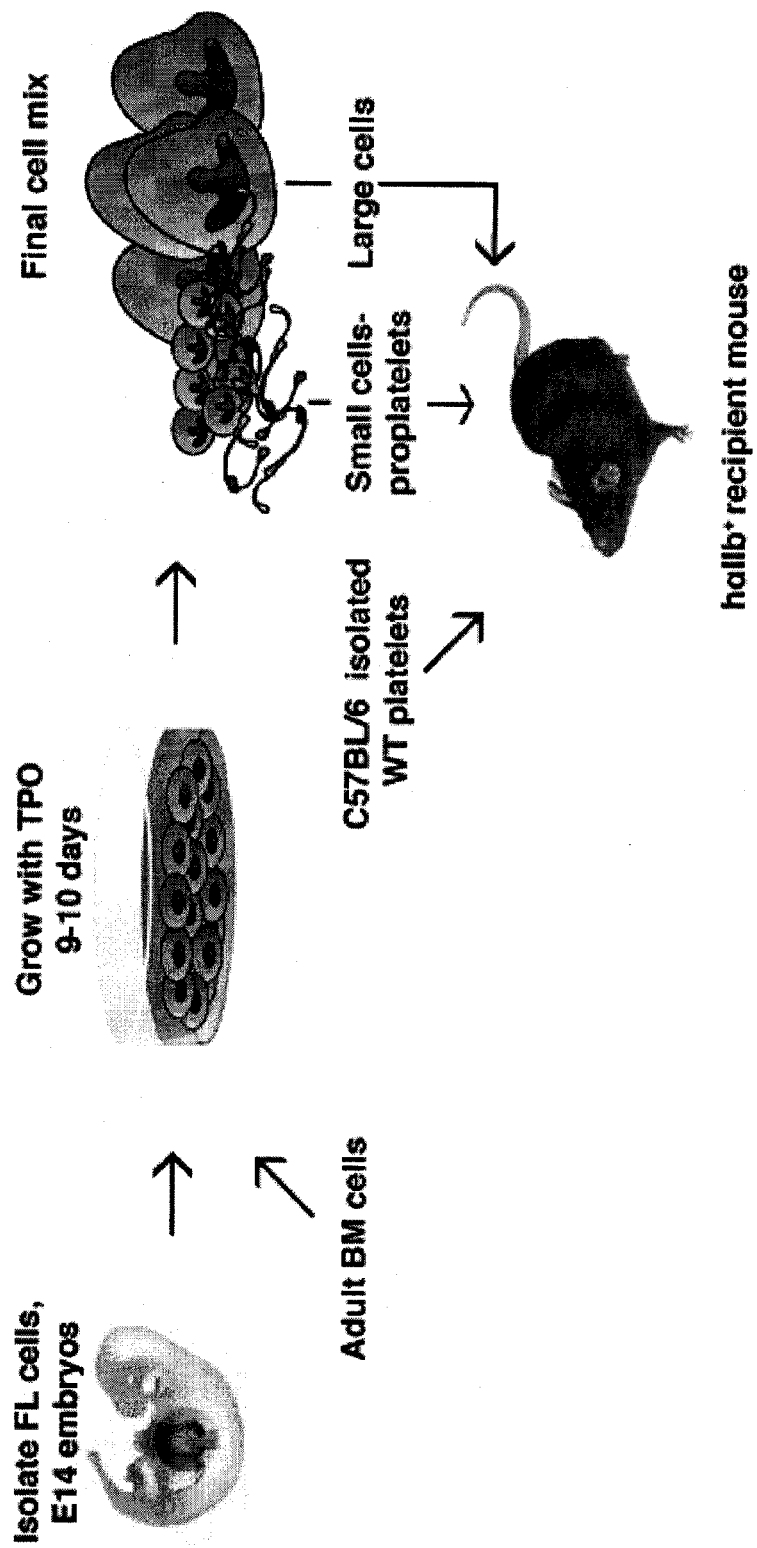
FIG. 1 is a schematic of the isolation of fetal liver (FL) and bone marrow (BM) derived megakaryocytes and infusing into a recipient mouse. Three different products for infusion were collected: isolated wildtype (WT) platelets, large and small cells were obtained from FL cells grown in the presence of TPO. These were then infused into mice that had human αIIb (hαIIb) as a marker on their platelet surface instead of mouse αIIb (maαIIb). Flow cytometric analysis of whole blood from hαIIb+ recipient mice before and at different time points after infusion of donor cells was performed. Blood was stained with labeled species-specific (mouse or human) anti-αIIb antibodies.

As explained above, current platelet transfusions are limited by their short storage half-life, variable quality and quantity, high-risk of bacterial contamination, and frequency of patients developing inhibitors to the transfused platelets. Present day efforts to develop platelets ex vivo have met with very limited and not clinically relevant results. The present invention provides compositions and methods for the generation of sufficient platelets (ex vivo or in vivo), particularly from ex vivo grown megakaryocytes infused into a recipient. In a particular embodiment, the platelets are derived from megakaryocytes derived from mammalian hematopoietic progenitor cells or iPS cells, particularly human embryonic stem cells (e.g., hESC). Herein, it was found that by infusing ex vivo generated murine megakaryocytes into mice, an approximately 100-fold increase in recipient platelet count was achieved over prior published results, thereby achieving clinically relevant levels of donor platelets. These platelets have a slightly shorter half-life than infused platelets, but are normal in size, expression of surface markers, and functionality. In similar studies of human ex vivo-generated megakaryocytes, the half-life is as good as or better than infused human platelets into an NSG mouse. Infused megakaryocytes appear to be trapped in the pulmonary bed, where they shed their cytoplasm. The instant invention also provides methods of delivering therapeutics to a patient (e.g., via platelets or megakaryocyte infusion). Such methods allow for targeted delivery of therapeutics, e.g., to sites of vascular injury. The methods and compositions of the instant invention may be used in place of present day platelet transfusions and these uses can be extended to new clinical situations using derived platelets that deliver targeted products for the treatment/inhibition/prevention of hemostasis, thrombosis, fibrinolysis, inflammation, angiogenesis, and the like. The methods of the instant invention are also readily scalable to allow for the large production of megakaryocytes and/or platelets. In turn, this means that the methods of the instant invention allow standardization of the platelets to be transfused, thereby increasing control over platelet reactivity and decreasing the incidence of resistance to platelet transfusion, while also avoiding issues related to bacterial contamination. The platelets derived by the instant methods are also "new" and better able to last after being generated in vivo.

In a particular embodiment of the instant invention, megakaryocytes and/or platelets are generated from stem cells, e.g., human ES and iPS cells. In another embodiment of the instant invention, the megakaryocytes are isolated from fetal liver or adult bone marrow.

In a particular embodiment of the instant invention, hematopoietic transcription factor GATA-1 (e.g., Gene ID: 2623) expression in hematopoietic progenitor cells, e.g., hESC, is markedly decreased or eliminated (e.g., by RNAi) in order to yield a self-replicating immortalized megakaryocyte-erythroid precursor (MEP)-like cell line G1ME (see, e.g., Stachura et al. (2006) Blood 107:87-97). GATA-1 expression may be decreased by conventional gene targeting (Shivdasani et al. (1997) EMBO J., 16:3965-73). For example, GATA1 may be deleted from the male human ES cell line H1 (NIH code WA01) through gene targeting (e.g., a knockout). As GATA1 is an X-linked gene, only a single round of targeting is required. Expression of GATA1 may also be down regulated (e.g., a knockdown) using antisense and/or RNAi (Gropp et al. (2007) Cloning Stem Cells 9:339-45). For example, GATA-1 antisense, siRNA, or shRNA (short hairpin RNA) or nucleic acid molecules encoding the same (e.g. via an expression vector, particularly a viral vector) may be delivered to the stem cells to reduce expression of GATA-1. As explained herein, the self-renewing MEPs may be modified that upon terminal differentiation into megakaryocytes, they store high levels of a protein of interest within their α-granules.

The re-induction of GATA-1 expression (particularly to or approximately to native levels) causes these MEPs to generate a large number of megakaryocytes. GATA-1 expression may be reactivated by delivering a nucleic acid molecule encoding GATA-1 to the cells, particularly via an expression vector (e.g., nucleofection) or a viral vector (e.g., lentiviral, retroviral, herpesviral, and adenoviral vectors), particularly a lentival vector), particularly under control of the native promoter (e.g., Hohenstein et al. (2008) Stem Cells 26:1436-43). In a particular embodiment, GATA-1 suppression by shRNA can be turned back on to its natural level by using a tetracycline-controlled transcriptional activation system (a tetracycline/Dox-Off system) (see, e.g., Gossen et al. (1992) Proc. Natl. Acad. Sci., 89: 5547-5551) or a Cre-lox system where the anti-GATA-1 shRNAs is flanked by lox sites and Cre recombinase expression is temporarily re-introduced in the cell to remove the shRNA construct.

Human megakaryocytes may be generated directly from stem cells, particularly hESC or iPS cells. In a particular embodiment, the GATA-1 deficient stem cells are cultured on stromal cells (e.g., OP9 stromal cells) in the presence of cytokines such as thrombopoietin (TPO) (Gaur et al. (2006) J. Thromb. Haemost., 4:436-42; Takayama et al. (2008) Blood 111:5298-306). When grown in the presence of TPO and OP9 cells, the stem cells become OP9 independent/TPO-dependent and have properties of a MEP cell. ~60% of these G1ME cells, upon re-expression of GATA-1, develop into identifiable megakaryocytes.

In another embodiment of the instant invention, the stem cells are differentiated into megakaryocytes via an embryoid body (EB)-based protocol in serum free conditions (Nostro et al. (2008) Cell Stem Cell 2:60-71; Yang et al. (2008) Nature 453:524-8). The EB protocol (see Examples) comprises formation of a primitive-streak-like population (stage 1), induction and specification of mesoderm (stage 2), and expansion of the megakaryocyte lineage (stage 3). Using this approach, hESC and iPS cell-derived EB generate a $KDR^{neg}/CD31^{pos}/CD41^{pos}$ population that displays megakaryocyte potential in vitro (French et al. (2007) Blood 110: Abstract 1265).

The megakaryocytes of the instant invention may be contacted with one or more agents to further stimulate or optimize platelet production. For example, megakaryocytes may be contacted at least one agent which enhances proplatelet formation such as a Src kinase inhibitor (e.g., SU6656) and/or prostaglandin J2 (Gandhi et al. (2005) Blood Cells Mol. Dis., 35:70-3; Akbiyik et al. (2004) Blood 104:1361-8). Megakaryocytes may also be contacted with/cultured with cytokines involved in megakaryocyte migration in niches, stromal-derived factor-1, fibroblast growth factor-1, vascular cell adhesion molecular-1, and the like (Avecilla et al. (2004) Nat. Med., 10:64-71). Megakaryocytes may also be contacted with a Rho/ROCK1 kinase inhibitor such as dimethylfasudil (diMF). The cells may also be cultured in specialized culture plates under conditions to simulate the pore size in the bone marrow vasculature.

Thrombocytopenic NSG mice may be used to study the cells/platelets of the instant invention (Newman et al. (2007) J. Thromb. Haemost., 5:305-9). For example, the thrombocytopenic NSG mice may be infused with the megakaryocytes generated by the methods of the instant invention. In this model, both quantitative (platelet count rise and half-life) as well as qualitative (quiescent platelets that can be appropriately activated) aspects of the new platelets may be measured. Studies may also be done in NSG mice that have normal platelet numbers. Two pathological thrombus models: 1) the $FeCl_3$ carotid artery injury (Gewirtz et al. (2008) J. Thromb. Haemost., 6:1160-6; Stachura et al. (2006) Blood 107:87-97) and 2) a photochemical stroke model (Eichenbaum et al. (2002) J. Pharmacol. Toxicol. Methods 47:67-71)) may be used to study the infused modified platelets, e.g., to determine if they can prevent and/or lyse pathologic thrombi.

In accordance with the instant invention, methods of treating, inhibiting and/or preventing thrombocytopenia and/or the bleeding diathesis associated with the thrombocytopenia are provided. The methods comprise administering megakaryocytes and/or platelets of the instant invention to a subject in need thereof. Thrombocytopenia is any disorder in which there is an abnormally low amount of functional platelets, e.g., it is a condition wherein the concentration of platelets in the blood of a patient is below what is considered normal for a healthy patient (e.g., 150 and 400 million per milliliter of blood is typically considered normal). The decrease in platelet number in the individual can be, for example, a decrease in more than 20%, 30%, 40%, 60%, 80%, 90%, 95% or even more. The decreased platelets numbers may be due, for example, to decreased platelet production or increased platelet destruction.

Thrombocytopenia includes infection-induced thrombocytopenia, treatment-induced thrombocytopenia, and others. Thrombocytopenia may also be idiopathic. "Infection-induced thrombocytopenia" is thrombocytopenia which is caused by an infectious agent such as a bacteria or virus. "Treatment-induced thrombocytopenia" is thrombocytopenia that is caused by therapeutic treatments such as chemotherapy (chemotherapy induced thrombocytopenia), radiation treatment (e.g., gamma irradiation, therapeutic exposure to radiation), and exposure to certain drugs such as, without limitation, cytotoxic drugs, chemicals containing benzene or anthracene, chloramphenicol, thiouracil, and barbiturate hypnotics. Other types of thrombocytopenia include, without limitation, those resulting from bone marrow failure (e.g., rare bone marrow disorders such as congenital amegakaryocytic hypoplasia and thrombocytopenia with absent radii (TAR syndrome), bone marrow transplantation, bone marrow cancer, and aplastic anemia), splenomegaly (e.g., caused by portal hypertension), liver disease (cirrhosis), macrophage storage disorders such as Gaucher's disease, autoimmune disorders such as idiopathic or immune thrombocytopenic purpura (ITP), vasculitis, hemolytic uremic syndrome, thrombotic thrombocytopenic purpura (TTP), disseminated intravascular coagulopathy (DIC), and prosthetic cardiac valves.

As discussed herein, the expression of at least one protein of interest (inclusive of polypeptides and peptides) within megakaryocytes can be used for different clinical uses. For example, modified megakaryocytes/platelets may be used for targeted hemostatic, fibrinolytic and angiogenic purposes. The protein of interest can be expressed in the megakaryocytes by delivering a nucleic acid molecule encoding the protein of interest to the megakaryocyte or a precursor such as the MEP cell or stem cell. The nucleic acid molecule may be contained within an expression vector, particularly a viral vector such as a lentiviral vector. The nucleic acid molecule of interest may be expressed in a megakaryocyte-specific manner (e.g., using a pBSK-based plasmid with the coding region of the protein of interest driven by a megakaryocyte-specific promoter like that of the GPIb alpha gene). In a particular embodiment, the nucleic acid molecule of interest is operably linked to the glycoprotein (GP) Ibα promoter. The vector comprising the nucleic acid molecule of interest may be delivered to the cell (e.g., ES or iPS cell, MEP cell, or megakaryocyte) via any method (e.g., transfection, infection, electroporation, etc.). In a particular embodiment, clones which express the protein of interest at a high level per final megakaryocyte are selected.

Examples of proteins of interest which can be expressed in megakaryocytes include, without limitation:

1) Fibrinolytic agents, thrombolytic agent, or anti-thrombotic agents may be used to lyse thrombi (in vivo). In a particular embodiment, the anti-thrombotic platelets effectively lyse thrombi in vivo without causing systemic changes such as decreased fibrinogen levels or the generation of fibrin degradation products. Examples of fibrinolytic agents include, without limitation, urokinase (e.g., urinary plasminogen activator, uPA), tissue plasminogen activator (tPA) (e.g., alteplase, reteplase, tenecteplase), prourokinase, and streptokinase.

2) Procoagulant proteins may be used to treat, inhibit, and/or prevent bleeding (e.g., due to vascular injury), bleeding disorders, or bleeding diathesis. For example, Factor VIII (FVIII) may be delivered via the cells of the instant invention for the treatment of hemophilia A. Examples of procoagulant proteins include, without limitation, FVIII and Factor IX. Examples of bleeding disorders to be treated include, without limitation, hemophilia A, hemophilia B, coagulation factor deficiency (e.g., FVII, FIX, FX, FXI, FV, FXII, FII, vWF), vitamin K epoxide reductase C1 deficiency, gamma-carboxylase deficiency, and bleeding associated with, e.g., trauma, injury, thrombocytopenia, and over-treatment with anticoagulants.

3) Anti-angiogenic agents or chemotherapeutic agents may be used to treat, inhibit, and/or prevent cancer (e.g., blood cancers such as leukemias, lymphomas, etc.). In a particular embodiment, the anti-angiogenic agent or chemotherapeutic agent is used to treat, inhibit, and/or prevent metastasis, such as metastasis in CIT. Examples of anti-angiogenic agents include, without limitation, soluble vascular endothelial growth factor (VEGF) receptor (serf), neuropilin-1 (NRP-1), angiopoietin 2, thrombospondin 1, thrompospondin 2, angiostatin, endostatin, vasostatin, calreticulin, platelet factor-4, cartilage-derived angiogenesis inhibitor, tissue inhibitors of metalloproteinases (TIMP), interferon ($\alpha$, $\beta$, or $\gamma$), interleukin (e.g., IL-4, IL-12, IL-18), prothrombin, prolactin, antithrombin III fragment, and vascular endothelial growth inhibitor (VEGI).

4) Anti-inflammatories may be used to treat, inhibit, and/or prevent vasculitis. As used herein, an anti-inflammatory refers to compounds for the treatment of an inflammatory disease or the symptoms associated therewith. In a particular embodiment, the anti-inflammatory is a peptide such as anti-inflammatory peptide 1.

I. DEFINITIONS

The following definitions are provided to facilitate an understanding of the present invention:

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" may refer to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

A "vector" is a replicon, such as a plasmid, cosmid, bacmid, phage or virus, to which another genetic sequence or element (either DNA or RNA) may be attached so as to bring about the expression and/or replication of the attached sequence or element.

The term "gene" refers to a nucleic acid comprising an open reading frame encoding a polypeptide, including exon and (optionally) intron sequences. The nucleic acid may also optionally include non-coding sequences such as promoter or enhancer sequences. The term "intron" refers to a DNA sequence present in a given gene that is not translated into protein and is generally found between exons.

Antisense molecules are oligonucleotides that hybridize under physiological conditions to a particular gene or to an mRNA transcript of such gene and, thereby, inhibit the transcription of such gene and/or the translation of such mRNA. The antisense molecules are designed so as to interfere with transcription or translation of a target gene upon hybridization with the target gene or its mRNA. Antisense molecules are typically between about 15 and about 30 nucleotides, but the exact length of the antisense oligonucleotide and its degree of complementarity with its target depend upon the specific target selected. An antisense oligonucleotide is preferably constructed to bind selectively with the target nucleic acid under physiological conditions. Antisense molecules may span the translational start site of mRNA molecules. Antisense constructs may also be generated which contain the entire gene sequence in reverse orientation. Antisense oligonucleotides targeted to any known nucleotide sequence can be prepared by oligonucleotide synthesis according to standard methods.

The term "siRNA" refers to small inhibitory RNA duplexes such as those that induce the RNA interference (RNAi) pathway. siRNA may vary in length, but are generally 12-30, more typically about 21 nucleotides in length (see, e.g., Ausubel et al., eds., Current Protocols in Molecular Biology, John Wiley and Sons, Inc.). siRNA may have unpaired overhanging bases on the 5' or 3' end of the sense strand and/or the antisense strand. As used herein, the term "siRNA" includes duplexes of two separate strands and single strand molecules that can form hairpin structures comprising a duplex region (shRNA).

The phrase "operably linked," as used herein, may refer to a nucleic acid sequence placed into a functional relationship with another nucleic acid sequence. Examples of nucleic acid sequences that may be operably linked include, without limitation, promoters, cleavage sites, purification tags, transcription terminators, enhancers or activators and heterologous genes which when transcribed and, if appropriate to, translated will produce a functional product such as a protein, ribozyme or RNA molecule. The phrase "operably linked" may also, for example, refer to a nucleic acid sequence encoding a protein of interest placed in functional relationship with a nucleic acid encoding the carboxy-terminal domain of a Ubl such that the catalytic cleavage activity of the carboxy-terminal domain of a Ubl in proteinaceous form leads to the release of the protein of interest.

The term "isolated" may refer to protein, nucleic acid, compound, or cell that has been sufficiently separated from the environment with which it would naturally be associated (e.g., so as to exist in "substantially pure" form). "Isolated" does not necessarily mean the exclusion of artificial or synthetic mixtures with other compounds or materials, or the presence of impurities that do not interfere with the fundamental activity, and that may be present, for example, due to incomplete purification.

The term "substantially pure" refers to a preparation comprising at least 50-60% by weight of a given material (e.g., nucleic acid, oligonucleotide, polypeptide, protein, cell, etc.). More preferably, the preparation comprises at least 75% by weight, and most preferably 90-95% by weight of the given compound. Purity is measured by methods appropriate for the given compound.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease or disorder, including improvement in the condition of the patient (e.g., in one or more symptoms), delay in the progression of the condition, etc.

A "therapeutically effective amount" of a compound or a pharmaceutical composition refers to an amount effective to prevent, inhibit, treat, or lessen the symptoms of a particular disorder or disease. The treatment of a disease or disorder herein may refer to curing, relieving, inhibiting, and/or preventing the disease or disorder, a symptom(s) of it, or the predisposition towards it.

The term "culturing" refers to growing or maintaining a population of cells under suitable conditions in a medium.

II. ADMINISTRATION

Compositions comprising at least one megakaryocyte and/or platelet of the instant invention and at least one pharmaceutically acceptable carrier are also encompassed by the instant invention.

The instant invention encompasses methods of treating thrombocytopenia and/or other diseases or disorders comprising the administration of a composition comprising at least one megakaryocyte and/or platelet of the instant invention and at least one pharmaceutically acceptable carrier to a patient in need thereof. The term "patient" as used herein refers to human or animal (particularly mammalian) subjects. For example, the platelets of the instant invention may be generated in vitro from the megakaryocytes of the instant invention and then administered to a subject. In another embodiment, the megakaryocytes of the instant invention are delivered directly to the subject and platelets are subsequently produced in vivo.

The megakaryocytes and/or platelets of the instant invention may be conveniently formulated for administration with any pharmaceutically acceptable carrier. For example, the viral vectors may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the megakaryocytes and/or platelets of the instant invention in the chosen medium may be varied and the medium may be chosen based on the desired route of administration of the pharmaceutical preparation. Except insofar as any conventional media or agent is incompatible with the megakaryocytes and/or platelets to be administered, its use in the pharmaceutical preparation is contemplated.

The dose and dosage regimen of the compositions according to the invention that are suitable for administration to a particular patient may be determined by a physician/veterinarian/medical specialist considering the patient's age, sex, weight, general medical condition, and the specific condition for which the megakaryocytes and/or platelets of the instant invention is being administered and the severity thereof. The physician/veterinarian/medical specialist may also take into account the route of administration, the pharmaceutical carrier, and the biological activity of the megakaryocytes and/or platelets.

Selection of a suitable pharmaceutical preparation will also depend upon the mode of administration chosen. The pharmaceutical preparation comprises the megakaryocytes and/or platelets of the instant invention preferably dispersed in a medium that is compatible with the site of injection.

Megakaryocytes and/or platelets of the instant invention may be administered by any method. In a particular embodiment, the megakaryocytes and/or platelets of the instant invention are administered by direct injection, particularly intravenous injection into the blood stream. Pharmaceutical preparations for injection are known in the art. If injection is selected as a method for administering the megakaryocytes and/or platelets, steps should be taken to ensure that sufficient amounts of the megakaryocytes and/or platelets reach their target cells to exert a biological effect.

Pharmaceutical compositions containing a megakaryocytes and/or platelets of the present invention as the active ingredient in intimate admixture with a pharmaceutically acceptable carrier can be prepared according to conventional pharmaceutical techniques. The carrier may take a wide variety of forms depending on the form of preparation desired for administration, e.g., intravenous.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of megakaryocytes and/or platelets of the instant invention may be determined by evaluating the toxicity of the cells in animal models. Various concentrations of megakaryocytes and/or platelets in pharmaceutical preparations may be administered to mice or other animals, and the minimal and maximal dosages may be determined based on the beneficial results and side effects observed as a result of the treatment. Appropriate dosage unit may also be determined by assessing the efficacy of the megakaryocyte and/or platelet treatment in combination with other standard drugs. The dosage units of megakaryocytes and/or platelets may be determined individually or in combination with each treatment according to the effect detected.

The following examples are provided to illustrate various embodiments of the present invention. The examples are illustrative and are not intended to limit the invention in any way.

EXAMPLE 1

Materials and Methods

Characterization of the Mice Studied

Donor cells and platelets were derived from C57BL/6 WT mice (The Jackson Laboratory) or mUK-transgenic mice, which ectopically express murine urokinase within megakaryocytes (Kufrin et al. (2003) Blood 102:926-933). Recipient mice were homozygously transgenic for hαIIb and null for the expression of platelet mouse αIIb (mαII−/−) (Thornton et al. (2002) Blood 100:3588-3596), designated hαIIb+ mice, and expressed 20% of the level of CD41 seen on human platelets (Wagner et al. (1996) Blood 88:907-914.). All animal studies were done with approval of the Institutional Animal Utilization Committee at the Children's Hospital of Philadelphia.

Isolation of Platelets and Megakaryocytes Ex Vivo

Figure 6:
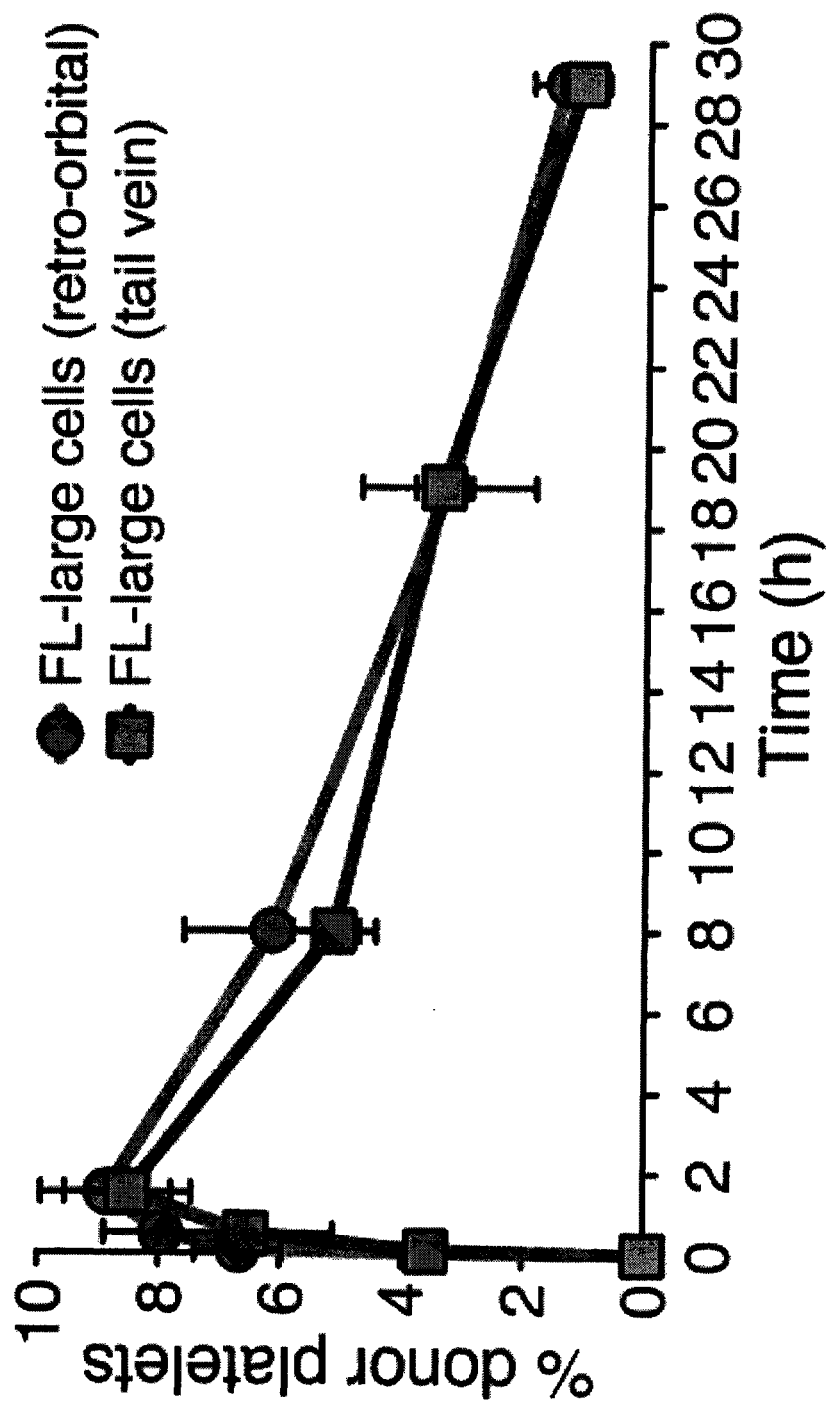
FIG. 6 shows a comparison of retro-orbital Vs tail vein infusions of FL-large cells. Flow cytometric percentage of infused ~$10^6$ FL-large cells in recipient animals. N=5 study per arm, Mean±1 standard deviation (SD) are shown. These studies show that the site of megakaryocyte infusion has no effect on platelet shedding.

Fetal liver (FL) megakaryocytes were obtained from E14 FL cells homogenized and cultured as previously described (Lecine et al. (1998) J. Biol. Chem., 273:7572-7578). Adult BM cells were obtained from femurs and tibiae of C57BL/6 mice (Shivdasani et al. (2005) Curr. Protoc. Immunol., Chapter 22:Unit 22F.6). Mature megakaryocytes were isolated using a 2-step density gradient (e.g., BSA step gradient 1.5% and 3%) (Shivdasani et al. (2005) Curr. Protoc. Immunol., Chapter 22:Unit 22F.6). Washed platelets derived from the inferior vena cava of C57BL/6 mice in acid citrate-dextrose were prepared as previously described (Zhang et al. (2001) Blood 98:610-617). Platelet counts were determined using a HemaVet® counter (Triad Associates). Platelets and/or megakaryocytes were infused into recipient mice retro-orbitally or by tail vein; the two approaches gave similar outcomes (FIG. 6).

Characterization of the Megakaryocytes

Megakaryocytes to proplatelet number was determined visually with a hemocytometer. DNA ploidy was assessed by flow cytometry after staining with propidium iodide using a FACScan™ (BD) as described previously (Kanaji et al. (2004) Blood 104:3161-3168).

Flow Cytometric Studies in Infused hαIIb+ Mice

Retro-orbital blood samples from recipient mice were double stained with monoclonal FITC-conjugated mouse anti-human CD41 Ab (eBioscience) and monoclonal phycoerythrin-conjugated (PE-conjugated) rat anti-mouse CD41 Ab (BD Biosciences) for 30 minutes and analyzed by flow cytometry. Activation of infused platelets was assessed by 3-color whole blood flow cytometry, using monoclonal mouse anti-human CD41 (PerCP-Cy5.5), PE-rat anti-mouse CD41, and monoclonal FITC-rat anti-mouse P-selectin Abs (all from BD Biosciences). To examine the relative expression of membrane receptors in recipient versus donor platelets, whole blood was stained with mouse anti-human CD41 (PerCP-Cy5.5), PE-rat anti-mouse CD41, and either monoclonal FITC-labeled rat anti-mouse GPIbα or rat anti-mouse GPIX Ab (Emfret Analytics).

Infusion Studies in Thrombocytopenic hαIIb+ Mice

Mice were subjected to a high dose of irradiation (1,000 centigrays total; two sessions, 24 hours apart). Platelet counts were initially monitored daily to determine a temporal platelet profile. Animals included in these studies had platelet counts between $1 \times 10^8$ to $2 \times 10^8$/ml on day 7 after irradiation and immediately before infusion of the cells in 200 μl CATCH buffer. Additional counts were done at 4, 24, and 48 hours after infusion.

Cremaster Laser Injury Functional Studies

One hour after cell infusion, recipient hαIIb+ male mice were studied in the cremaster laser injury model (Neyman et al. (2008) Blood 112:1101-1108). Anti-mouse CD41 Fab fragments labeled with Alexa Fluor 488 (Pierce Biotechnology) were injected intravenously 5 minutes before injury. Data were collected over a course of 2.5 minutes at 5 frames per second.

FeCl$_3$ Carotid Artery Injury Functional Studies

FeCl$_3$-induced arterial injury was induced in hαIIb+ mice 1 hour after infusion. Studies were done as previously described (Yarovoi et al. (2003) Blood 102:4006-4013), but the 20% FeCl$_3$ injury was for 3 minutes. Total flow was recorded for 30 minutes.

Infused Megakaryocyte Fate Studies

FL-derived cells were cultured for 5 days and then exposed to 10 μM BrdU (Sigma-Aldrich) for 48 hours prior to infusion. Following infusions, recipient mice were sacrificed and organs isolated, then fixed in formalin at predetermined time points. Detection of BrdU-labeled nuclei was performed with a rat polyclonal anti-BrdU Ab and a biotinylated rabbit polyclonal anti-rat IgG as the secondary Ab (Abcam), followed by a DAKO detection kit (EnVision). Megakaryocyte cytoplasm in the lungs was similarly studied using a goat polyclonal Ab against murine αIIb (Santa Cruz Biotechnology Inc.) and a secondary biotinylated rabbit polyclonal anti-goat IgG Ab (Abcam).

Statistics

Differences between groups were compared using 2-tailed Student's t test. Statistical analyses were performed using Microsoft Excel. Differences were considered significant when P values were 0.05 or less.

Results

Figure 2A:
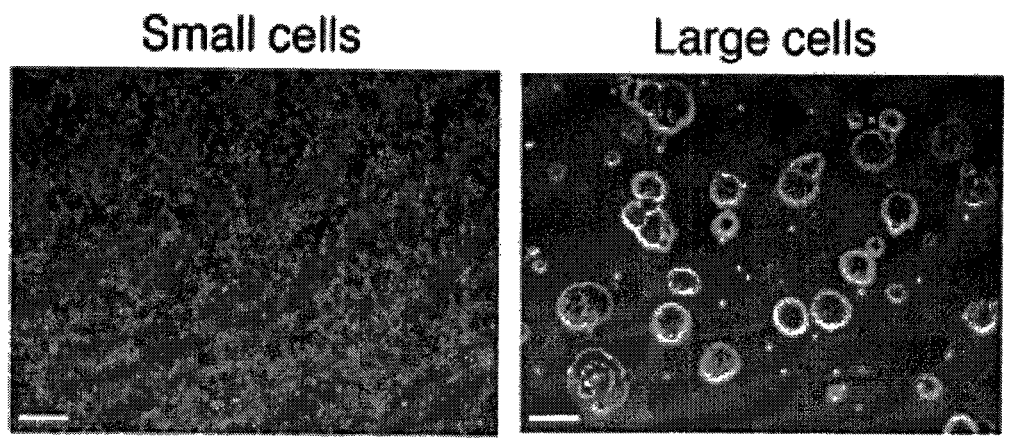
FIG. 2A provides representative fields of small and large cells. Scale bars: 100 μm.
Figure 2B:
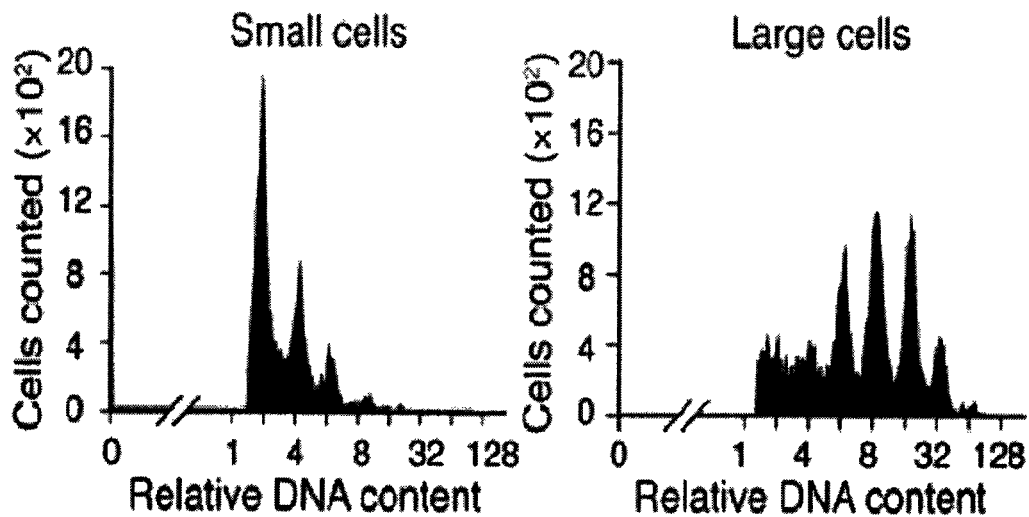
FIG. 2B provides representative analysis of DNA content of FL small and large cells.

To address whether infused megakaryocytes give rise to circulating platelets, fetal liver-(FL-) and BM-derived magakaryocytes were generated (FIG. 1) (Lecine et al. (1998) J. Biol. Chem., 273:7572-7578). Mature megakaryocytes were separated from other cells and proplatelets using a 2-step density gradient to produce "large cells," with more than half possessing a diameter greater than 50 μm and with only approximately 2.5:1 proplatelets/cell (FIG. 2A). The remaining "small cells" had approximately 10:1 proplatelets/cell (FIG. 2A). Ploidy analysis showed FL small cells with low DNA ploidy relative to FL large cells (FIG. 2B).

Figure 2C:
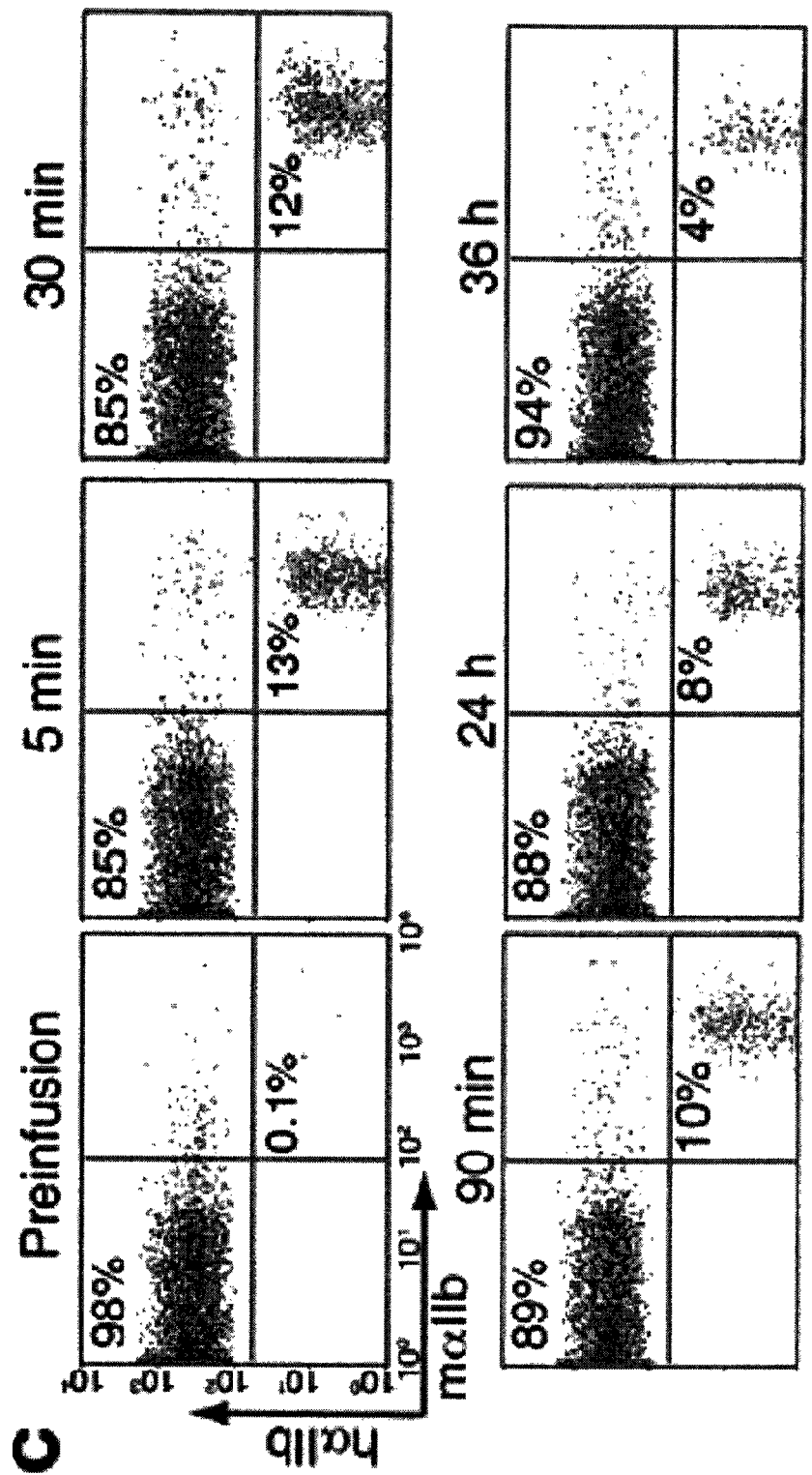
FIGS. 2C and 2D provide flow cytometry from recipient mouse before and after infusion of $10^8$ WT platelets (2C) or $10^6$ FL large cells (2D).
Figure 2D:
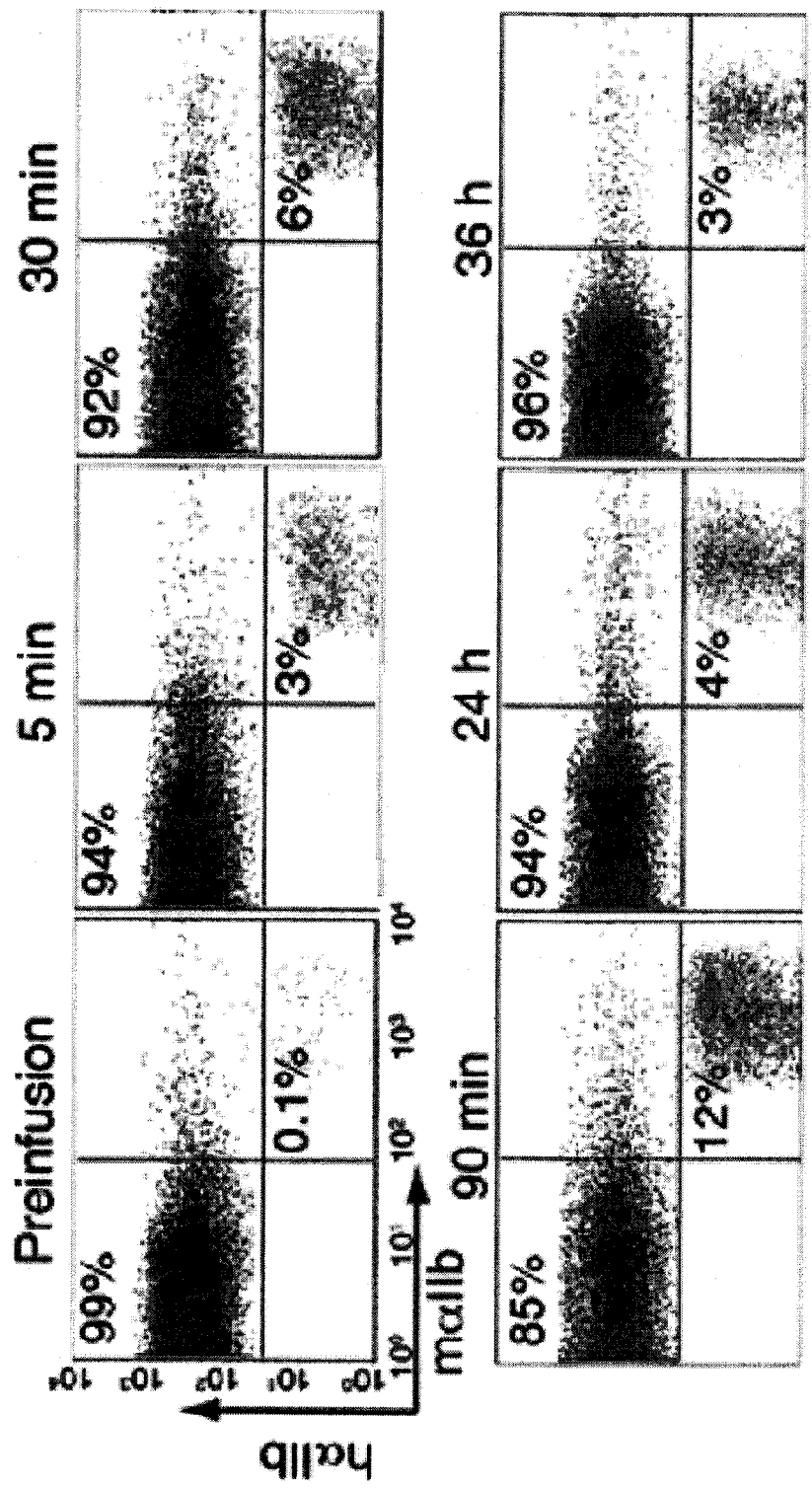
Figure 2E:
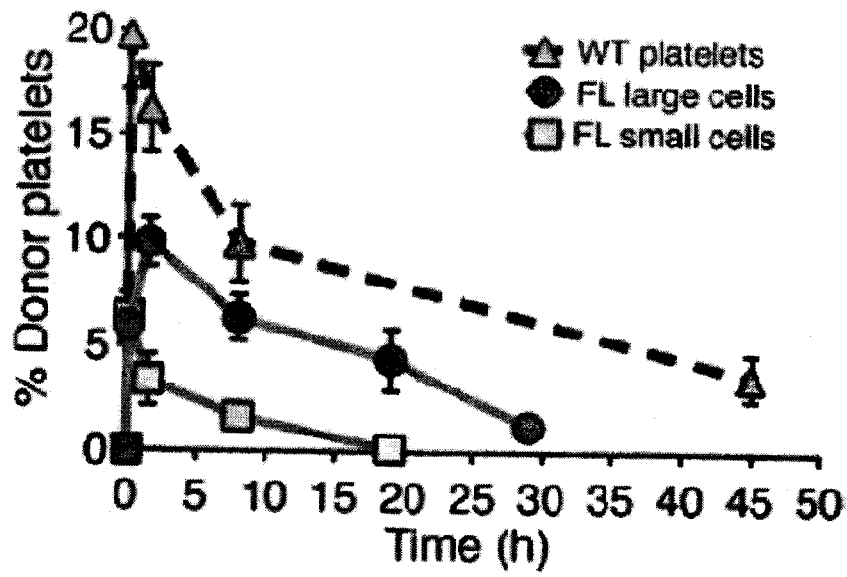
FIGS. 2E and 2F provide flow cytometric percentage of $10^6$ infused FL large cells (2E) and $10^6$ infused adult BM cells (2F). n=5 for WT platelets, n=9 for FL cells, n=5 for BM studies.
Figure 2F:
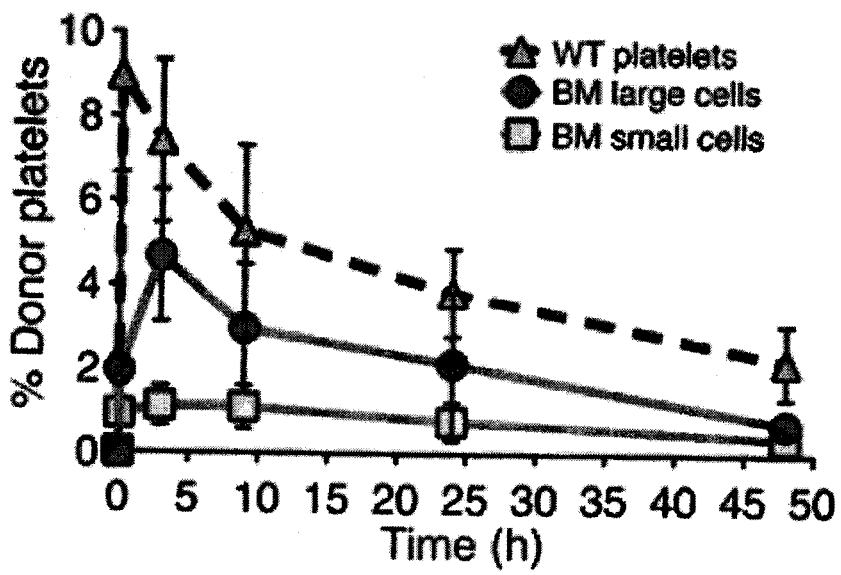
Figure 2G:
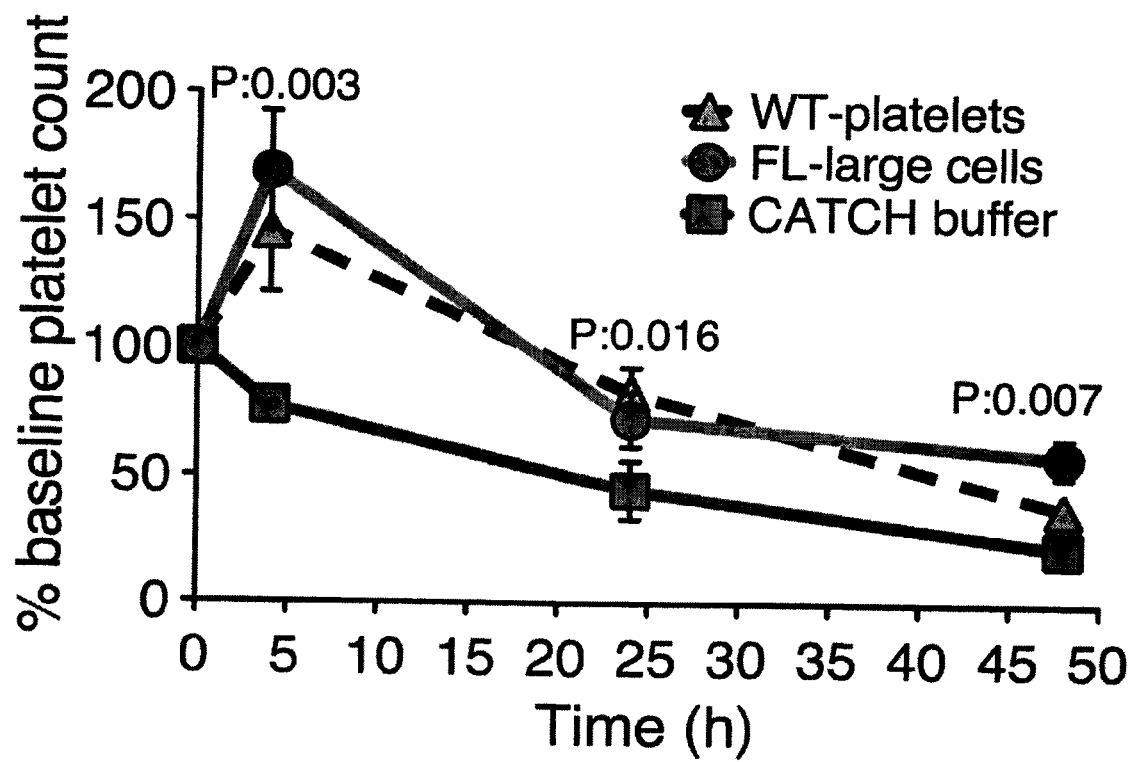
FIG. 2G provides percent platelet rise in irradiated thrombocytopenic mice after infusion. n=5 per arm. Mean±1 SD are shown. Initial platelet counts ($10^8$/ml) in the 3 groups were: CATCH buffer, 1.8±0.2; platelets, 1.9±0.3; large cells, 1.0±0.2.

Positive control WT platelets were isolated and infused into hαIIb+ recipient mice, with only human αIIb on their platelet surface (Thornton et al. (2002) Blood 100:3588-3596), to allow flow cytometric detection of infused platelets using species-specific anti-αIIb (CD41) Abs. After infusion, WT platelets were detected in hαIIb+ recipient mice immediately (i.e., 5-minute time point), with an overall half-life of approximately 36 hours (FIGS. 2C, 2E, and 2F). In contrast, infused FL large cells resulted in delayed platelets, with a peak at approximately 90 minutes (FIGS. 2D and 2E). These platelets had a shorter overall half-life of approximately 20 hours. Based on the number of cells infused, the peak increase in platelet count, and the recipient mouse blood volume of approximately 2 ml, it was calculated that 100-200 platelets from each large cell, assuming all cells gave rise to platelets. Infused FL small cells enriched with proplatelets gave rise to an immediate peak similar to infused WT platelets; however, these platelets had a truncated half-life of approximately 2 hours (FIG. 2E). Infusing adult BM megakaryocytes resulted in a similarly delayed appearance of platelets as with FL-derived megakaryocytes, but with a slightly longer half-life of 24 hours (FIG. 2F). To simulate clinical thrombocytopenia, mice were irradiated and infused CATCH buffer (1×PBS, 1.5% BSA, 1 mM adenosine, 2 mM theophylline, and 0.38% sodium citrate), WT platelets, or FL large cells near the induced platelet nadir. It was observed that both platelets and megakaryocytes significantly increased the platelet count relative to CATCH buffer over a time course of more than 24 hours (FIG. 2G).

Figure 2H:
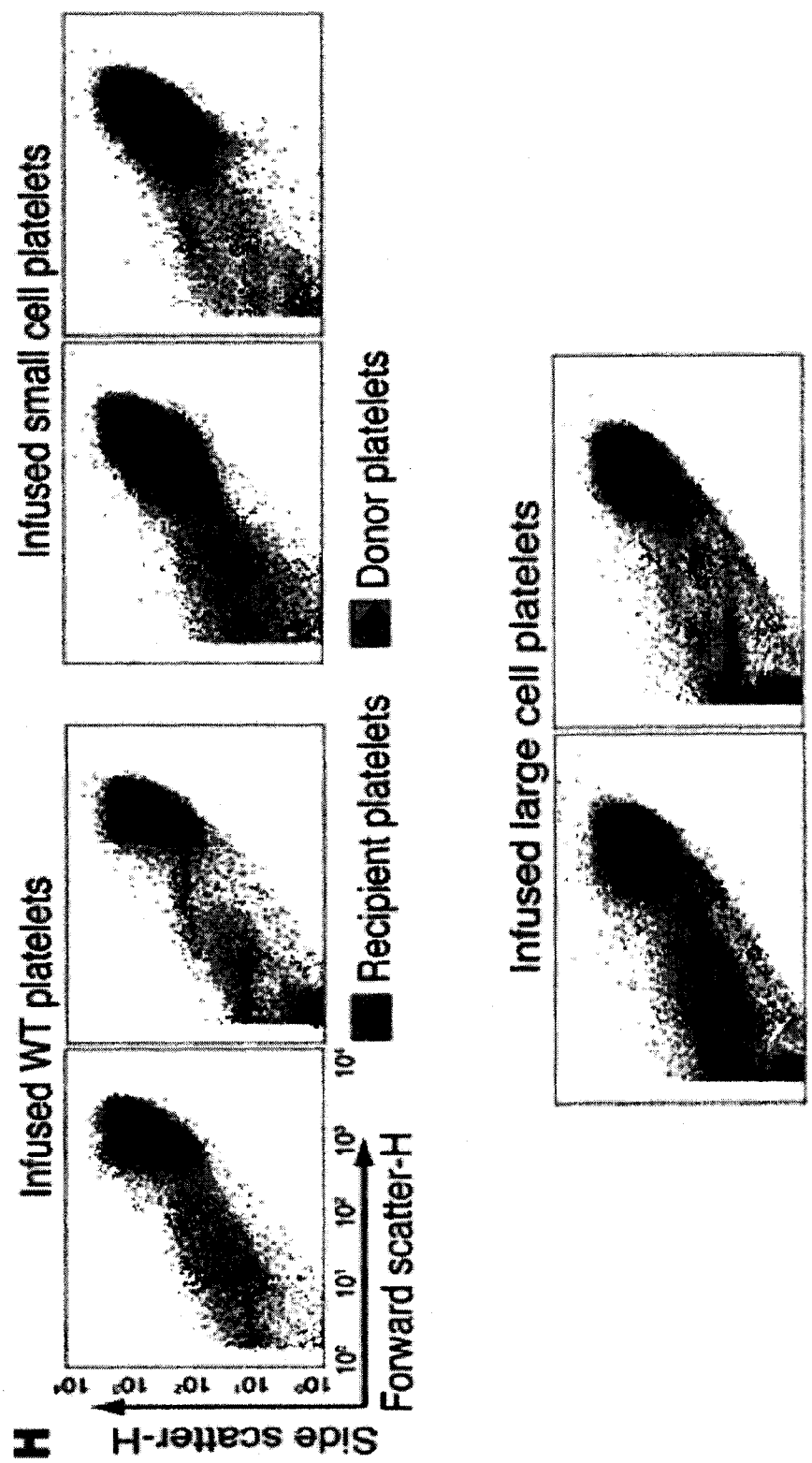
FIG. 2H provides the size determination of circulating recipient and infused platelets by forward versus side scatter analysis.
Figure 2I:
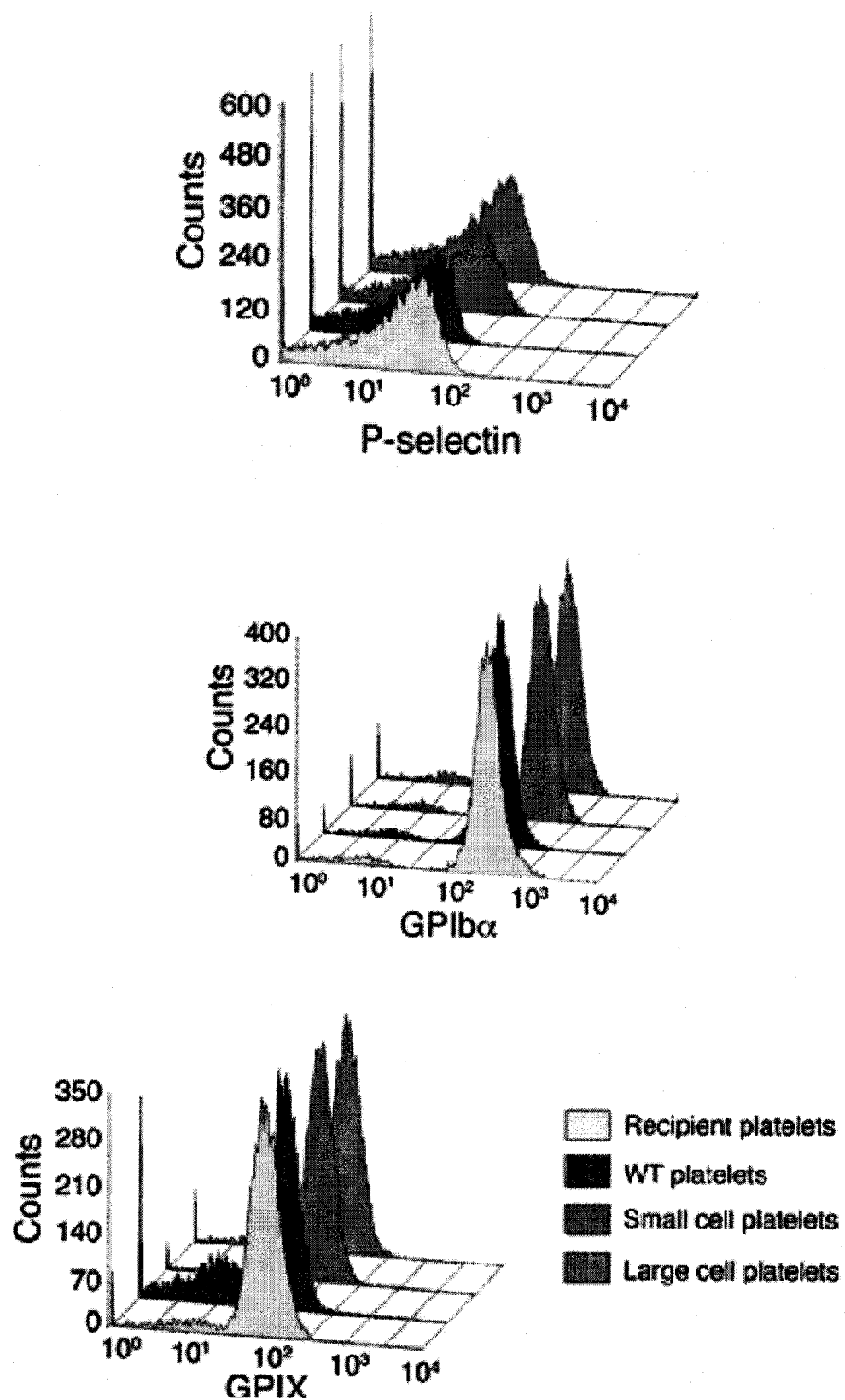
FIG. 2I provides representative flow cytometric analysis of infused and FL-derived platelets comparing surface expression of P-selectin, GPIbα, and GPIX.

To understand the shortened half-life of platelets derived from infused large cells, their size distribution was examined and microparticles were compared with infused WT platelets and no differences were found (FIG. 2H). Another indicator of platelet activation is the expression of surface P-selectin (Hsu-Lin et al. (1984) J. Biol. Chem., 259:9121-9126). Flow cytometric analysis showed that surface P-selectin levels were similar in platelets derived from infused FL cells and infused WT platelets (FIG. 2I). ADAM17 is a metalloproteinase found in cultures that shortens platelet half-life (Bergmeier et al. (2004) Circ. Res., 95:677-683) and cleaves the glycocalicin extracellular portion of GPIbα, inactivating the GPIb/IX receptor without altering receptor density (Bergmeier et al. (2003) Blood 102:4229-4235). Platelets derived from infused FL cells and infused WT platelets displayed similar ratios of extracellular GPIb to GPIX (FIG. 2I). Thus, the slightly shortened half-life of the platelets derived from infused large cells does not appear to be due to ADAM17 activity.

Figure 3A:
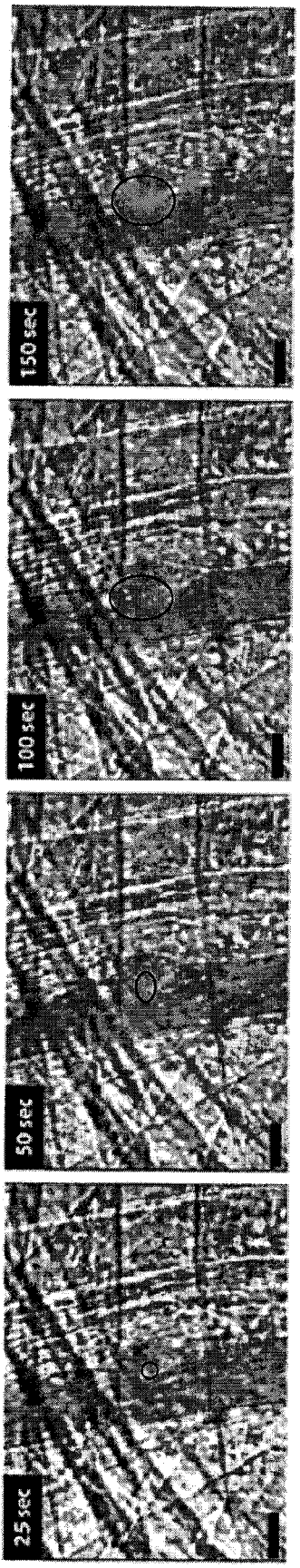
FIGS. 3A-3C provide representative images of platelets incorporating into clots after infusion of platelets or indicated cells (collections of cells are circled). Donor WT platelets were detected using a labeled anti-mouse αIIb Ab, optionally after infusion of FL cells.
Figure 3B:
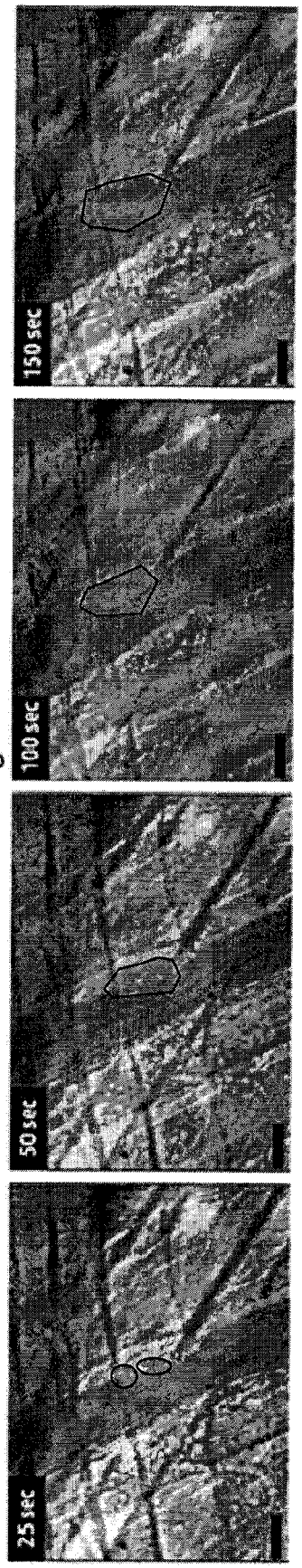
Figure 3C:
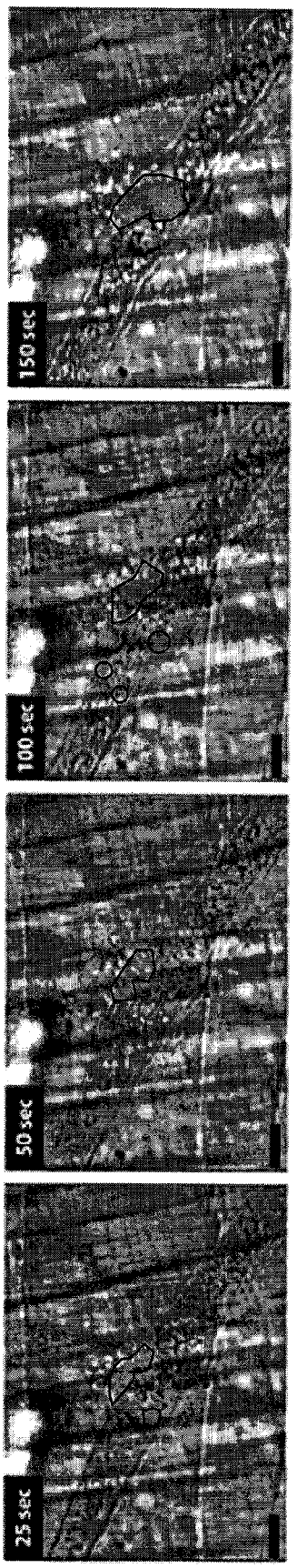
Figure 3D:
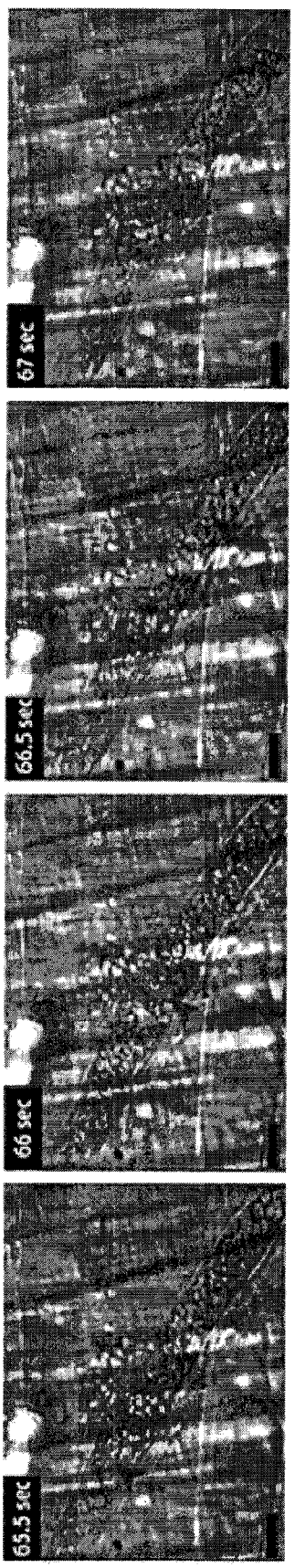
FIG. 3D provides sequential stills from left to right noting a recirculating mouse αIIb+ cell (arrowheads) after small cell infusion. Scale bars: 30 μm.
Figure 3E:
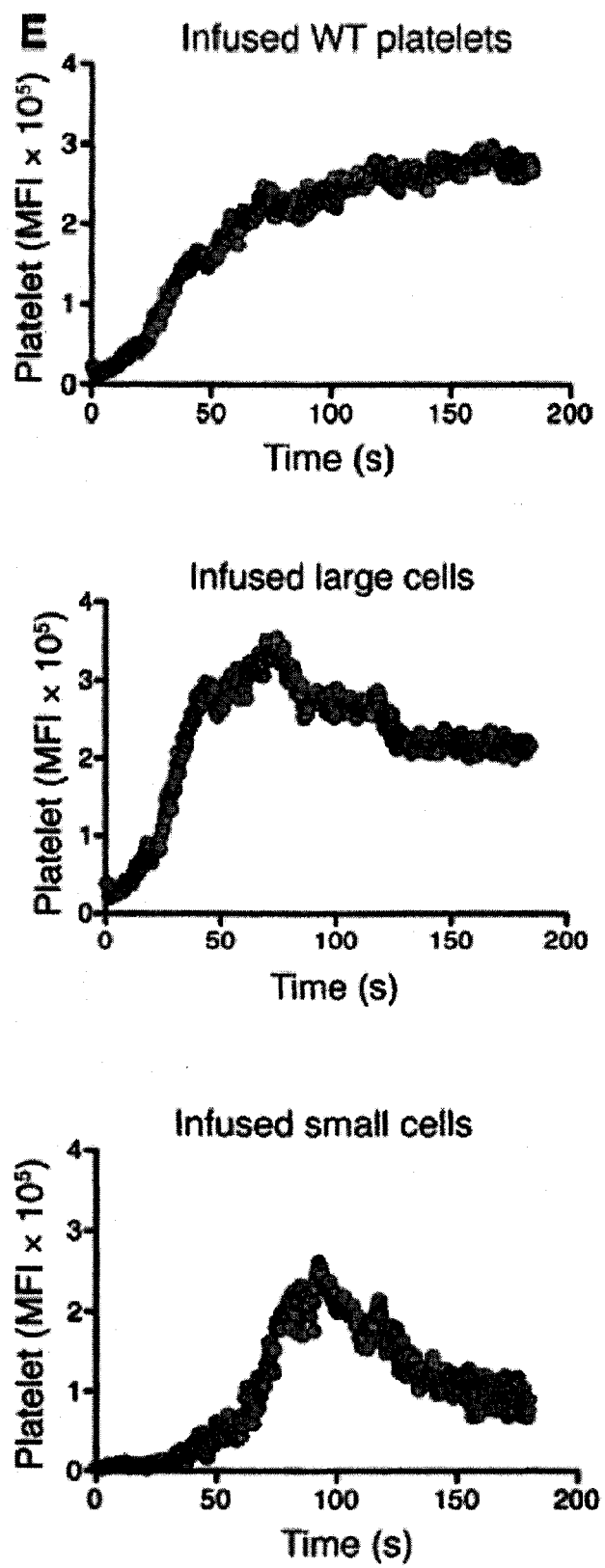
FIG. 3E provides a summation of donor platelets incorporated into growing thrombi after infusion of either WT platelets or FL cells. Twenty movies were evaluated per graph.

Clinically, platelets are typically transfused not to increase platelet number, but to reverse or prevent a bleeding diathesis due to thrombocytopenia. In the laser-induced cremaster arteriole injury model, incorporation of infused WT platelets and platelets derived from infused FL cells into growing clots was examined. In all settings, the platelets readily become incorporated into the developing thrombi. WT platelets and platelets derived from FL large cells were similarly incorporated (FIGS. 3A and 3B). Platelets derived from FL small cells incorporated to a lesser extent, with a distinct population of CD41+ cells that recirculated and rarely incorporated into the clot (FIGS. 3C and 3D). This phenomenon was rarely seen after infusion of FL large cells (FIG. 3B), and never with infused WT platelets (FIG. 3A).

Platelet function using an FeCl$_3$ carotid artery injury model was also examined after infusing either CATCH buffer or FL large cells into the hαIIb+ recipient mice, which have a mild bleeding diathesis likely because of low CD41 surface density (Wagner et al. (1996) Blood 88:907-914). Infusion of FL large cells significantly shortened time to development of stable occlusion (Table 1). FL large cells from mUK mice were also infused, which ectopically express and store urokinase in their α-granules (Kahr et al. (2001) Blood 98:257-265) and are resistant to thrombosis in the FeCl$_3$ carotid artery injury model. Transfusion of mUK platelets into WT mice blocked clot development (Kufrin et al. (2003) Blood 102: 926-933). It was reasoned that if infused mUK platelets from FL large cells are functional, they would interfere with clotting in the hαIIb+ recipient mice. Indeed, infused mUK large cells failed to form stable occlusions (Table 1).

TABLE 1

Effects of infused large cells in the FeCl$_3$ thrombosis model.

| Donor | Time to Occlusion (min) | Initial Occlusion (%) | Occluded at 30 min (%) | Blood Flow (ml/min) |
|---|---|---|---|---|
| Buffer | 7.4 ± 0.9 | 5/5 (100%) | 5/5 (100%) | 4.2 ± 1 |
| WT large cells | 5.3 ± 0.5[A] | 5/5 (100%) | 5/5 (100%) | 3.3 ± 1[A] |
| mUK large cells | >30 | 0/5[A] | 0/5[A] | 15.7 ± 1[A] |

[A]P < 0.03 compared with CATCH buffer infusion.

Figure 4A:
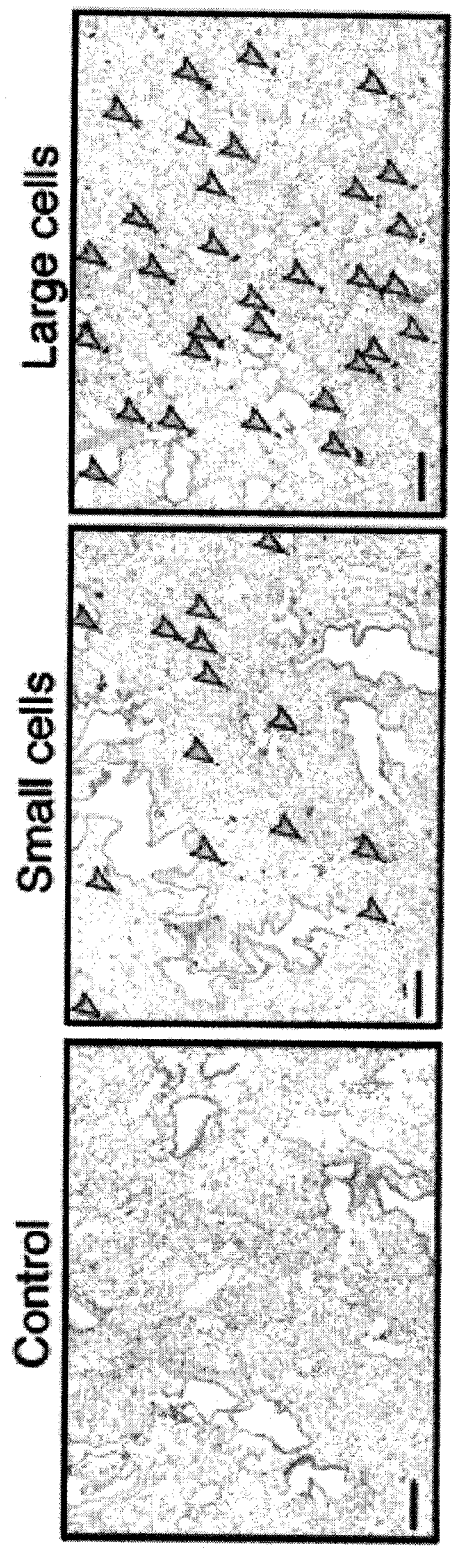
FIG. 4A shows staining of lung from hαIIb+ mice infused with saline or small or large cells grown in BrdU (arrows point to stained nuclei).
Figure 4B:
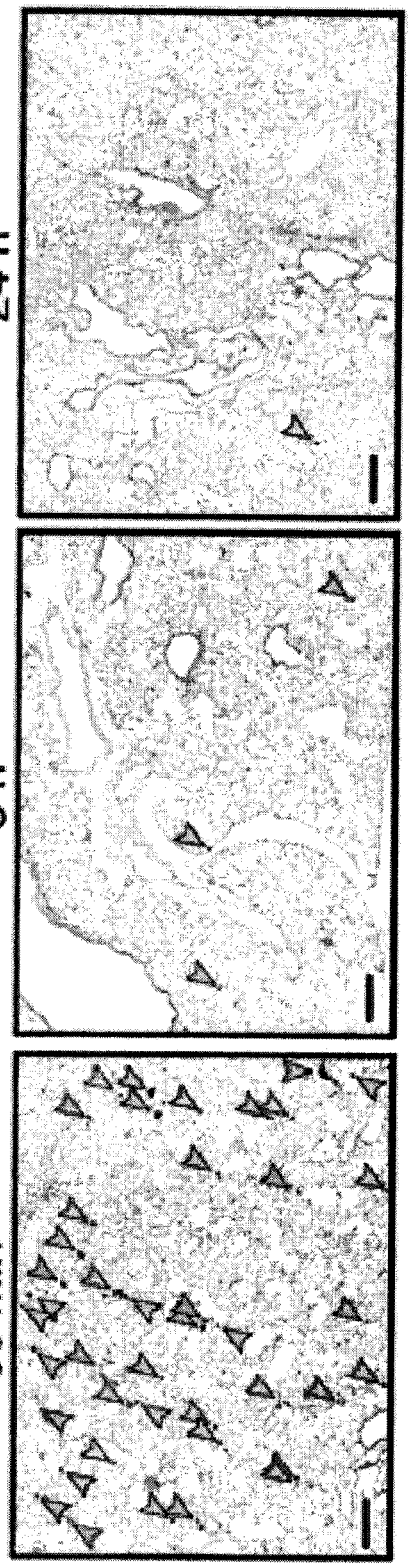
FIG. 4B shows the kinetics of BrdU-labeled large cells in the lungs.
Figure 4C:
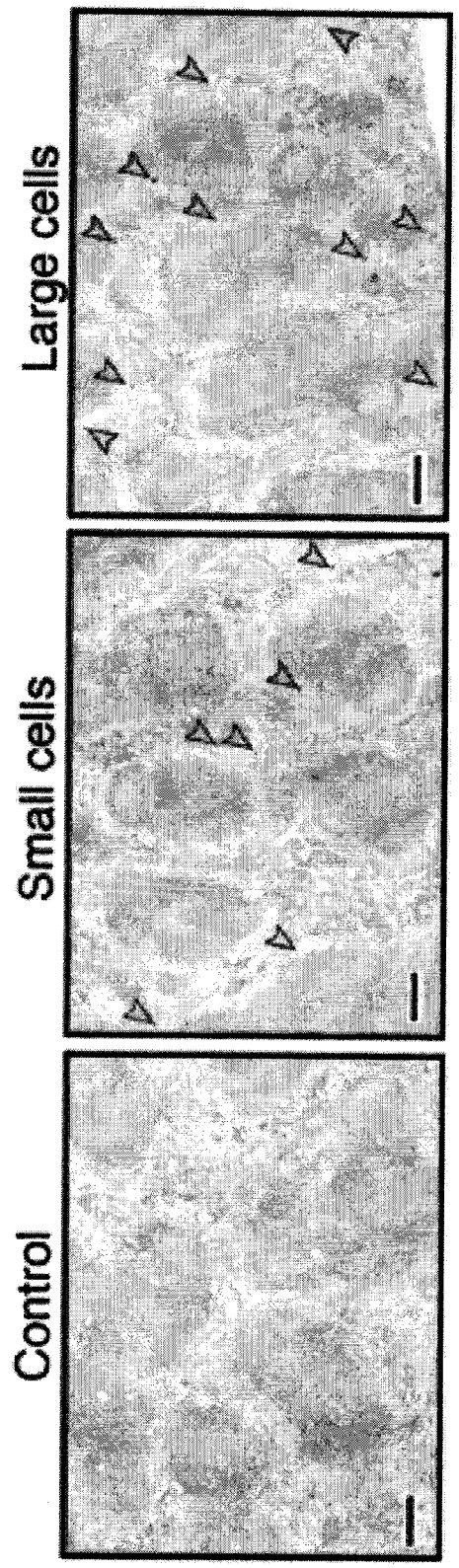
FIG. 4C shows staining of spleen from hαIIb+ mice infused with saline or small or large cells grown in BrdU (arrows point to stained nuclei). Scale bars: 200 μm.
Figure 4D:
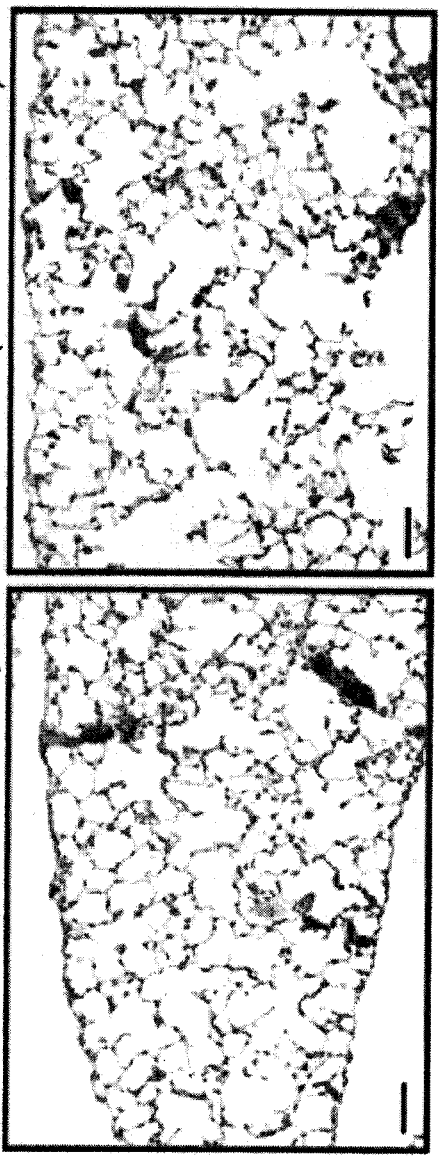
FIG. 4D shows large FL cells 30 minutes after infusion in lungs: BrdU-labeled nuclei (left) and man (right), Scale bars: 50 μm. Data are representative of 3 separate studies.

To begin to address where infused megakaryocytes shed platelets, megakaryocyte nuclei were labeled with BrdU. Various organs were isolated up to 36 hours after infusion. Virtually all of the BrdU-stained nuclei were in the lungs (FIG. 4A). Stained nuclei were visible for up to 24 hours (FIG. 4B). A few nuclei were visible in the red pulp of the spleen (FIG. 4C). None were present in the liver, heart, brain, or BM. The BrdU-labeled large cells appear to retain their cytoplasm for up to 30 minutes after infusion in pulmonary microvessels (FIGS. 4B and 4D), consistent with the delay in peak platelet count after infusion of FL large cells. To confirm this observation, the tissues were stained with an anti-murine CD41 Ab and detected positively stained cytoplasm up to 30 minutes (FIG. 4D). The studies and prior histological studies (Zucker-Franklin et al. (2000) Am. J. Pathol., 157:69-74) indicate that platelets can be released from circulating, mature, high-ploidy megakaryocytes directly within the vascular bed. Given the recent study showing megakaryocytes shedding large cytoplasmic fragments at the vascular niche in the marrow (Junt et al. (2007) Science 317:1767-1770), both large cytoplasmic fragments and whole megakaryocytes may escape into the vascular system and shed platelets within the pulmonary bed using mechanisms consistent with those revealed by in vitro studies (Italiano et al. (1999) J. Cell. Biol., 147:1299-1312), but with concurrent flow and local vascular factors involved as well (Dunois-Larde et al. (2009) Blood 114:1875-1883).

One would expect that megakaryocytes lodging in the lungs might pose a cardiovascular challenge. However, based on calculations shown in Table 2, only 0.4%-1.7% of the entire alveolar capillary bed were blocked. In addition to the capacity of the pulmonary vasculature to handle an influx of megakaryocytes, another question is whether this bed is specialized for platelet release. Individuals with significant right to left cardiovascular shunts are known to have lower platelet counts, which others have proposed to result from pulmonary bypass by circulating megakaryocytes (Lill et al. (2006) Am. J. Cardiol., 98:254-258). However, in fetal circulation, where one naturally bypasses the pulmonary bed, platelets are present (Van den Hof et al. (1990) Am. J. Obstet. Gynecol., 162:735-739).

TABLE 2

Calculation of number of alveoli capillaries blocked by infused megakaryocytes.

Mice platelet content: 1-2 × 10$^9$ platelets (Schmitt et al. (2001) Exp. Hematol., 29: 1295-1302)
Mice platelet half-life: 37 hours (Baker et al. (1997) Am. J. Hematol., 56: 17-25) Megakaryocyte sheds 10$^2$ platelets (determined in this study).
Calculate: 2-4 × 10$^6$ megakaryocytes each day traveling to the lungs to maintain the animal's platelet count.
Mice alveoli: 2.3 × 10$^6$ in both lungs (Knust et al. (2009) Anat. Rec., 292: 113-122)
Capillaries per alveoli: 25-100; based on human alveolar structure, corrected for the difference in volume between human and murine alveoli) (Weibel et al. (1962) Science 137: 577-585)
Calculate: Infusion of = 10$^6$ megakaryocytes over 10 minutes into the mice will block 0.4-1.7% of the entire capillary bed for a 24 hour period.

Figure 5A:
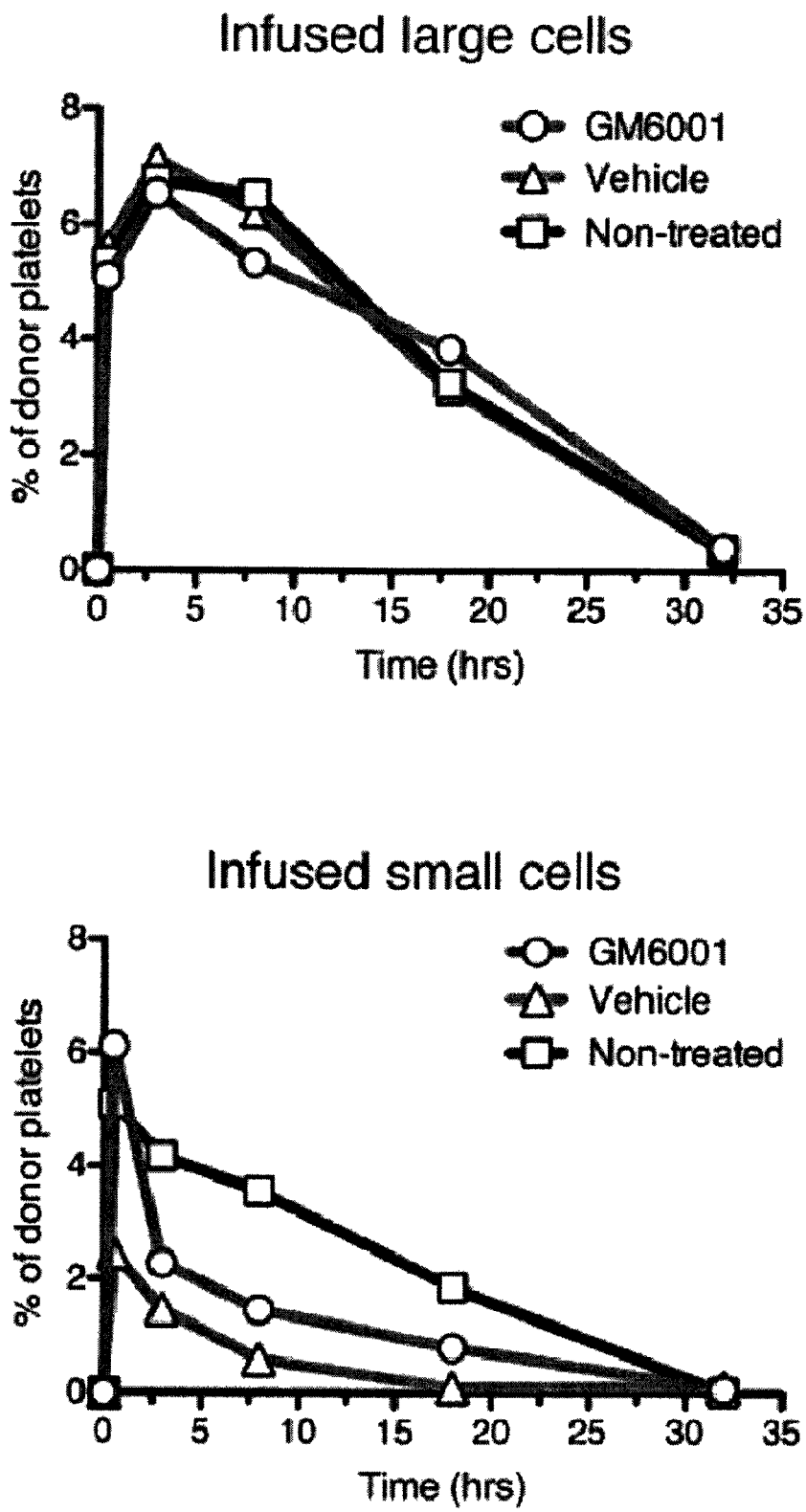
FIG. 5 shows that there is no metalloproteinase damage to shed platelets generated from ex vivo grown megakaryocytes. WT FL-cells were grown in culture in the presence of either metalloproteinase inhibitor GM6001 (100 μM, FIG. 5A) or TAP-1 (10 μM, FIG. 5B) and then separated into small and large cells and infused into hαIIb+ recipient mice to see if the metalloproteinase inhibitors improved the shorten half-life observed with non-treated derived platelets. N=2, performed in duplicates.
Figure 5B:
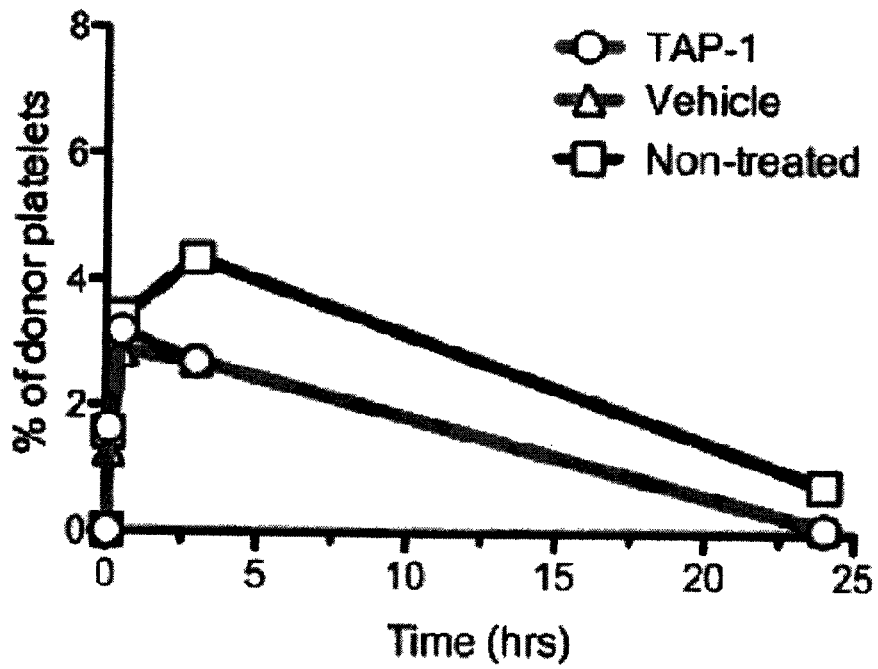
Figure 5B:
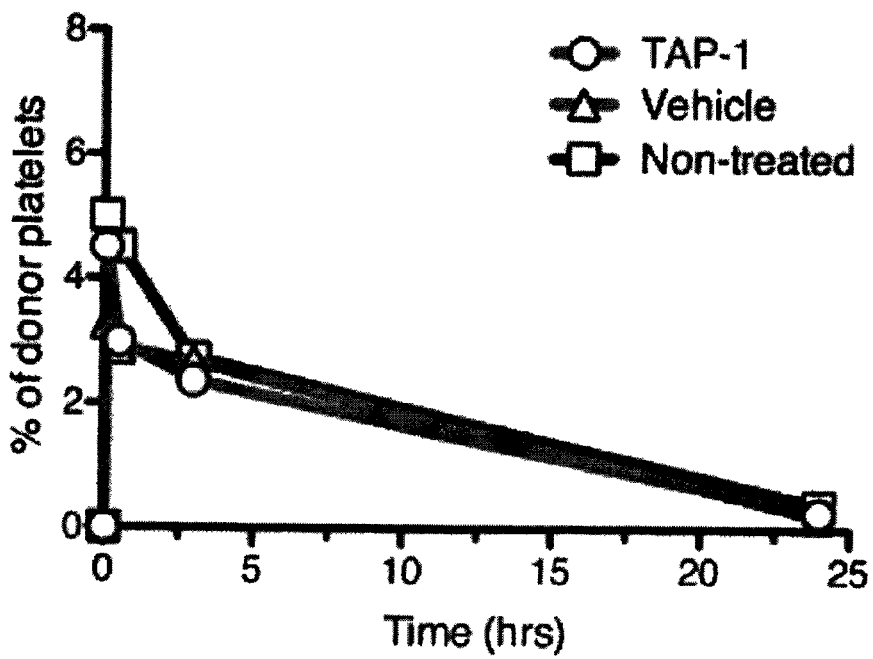

It has been shown herein that derived platelets from infused megakaryocytes are normal in size and expression of surface receptors and can be incorporated into growing thrombi. Previously, it had been suggested that ADAM17 is present in the media and shortens ex vivo generated platelet half-life (Nishikii et al. (2008) J. Exp. Med., 205:1917-1927). The instant studies showed no change in derived platelet half-life after megakaryocytes were grown in the presence of two inhibitors of ADAM 17, GM6001 and TAP-1 (FIGS. 5A and 5B). An alternative explanation for the shortened half-life is that most of the studies were performed with FL megakaryocytes, and fetal platelets have a shorter half-life compared with adult platelets (Jilma-Stohlawetz et al. (2001) Br. J. Haematol., 112:466-468). However, cultured infused adult BM megakaryocytes produced a similar delay in appearance and only a mildly longer half-life (FIG. 2F).

In vitro generation of a large number of biologically responsive platelets has remained problematic. The instant studies show that a human cell line can be established, expanded and differentiated into megakaryocytes, leading to a non-donor-dependent source of platelets. Such a line exists from mice: G1ME cells, which are derived from GATA-1-deficient embryonic stem cells and form approximately 50% megakaryocytes after re-expression of GATA-1 (Stachura et al. (2006) Blood 107:87-97). Modification of such lines to ectopically express a protein of interest during megakaryopoiesis would then be useful for targeted delivery of ectopic protein to sites of injury (Yarovoi et al. (2003) Blood 102: 4006-4013). This additional benefit of generating modified platelets in vivo from infused modified megakaryocytes is supported by studies showing efficacious, targeted urokinase delivery by platelets derived from mUK mouse megakaryocytes (Table 1).

Infused megakaryocytes can release platelets within the pulmonary bed and biologically active platelets can be formed in vivo with characteristics similar to those of normal platelets. The process is vigorous, and enough platelets are formed so that platelet count can be boosted and hemostasis can be improved and modified by targeted delivery of ectopic proteins. Based on the estimate of 100-200 platelets generated per infused megakaryocyte, $10^9$ mature megakaryocytes may be generated to achieve a 10% rise in platelet count in an average 70-kg patient.

EXAMPLE 2

Establishing a Self-Replicating Murine MEP Cell

Murine GATA-1 null ES cells were created and used to show that the GATA-1 transcription factor is critical for both erythroid and megakaryocyte development (Shivdasani et al. (1997) EMBO J., 16:3965-73). Growth of these cells for 2 weeks in the presence of OP9 stromal feeder cells and thrombopoietin (TPO) led to a self-renewing cell line G1ME. Such a self-replicating cell line was not seen using wildtype (WT) ES cells of the same strain (Stachura et al. (2006) Blood 107:87-97). When transfected with a retrovirus that led to expression of both GATA-1 and green fluorescent protein (eGFP), ~60% G1ME cells differentiated into megakaryocytes (GPIbα expression for mature megakaryoctes).

EXAMPLE 3

Generation of hESC-Derived Megakaryocytes

A 3-step embryoid body (EB)-based protocol in serum-free conditions to differentiate hESC lines into megakaryocytes has been used (French et al. (2007) Blood 110: Abstract 1265). Protocols for growth, maintenance, and differentiation of hESC lines have been described (Kennedy et al. (2007) Blood 109:2679-87). For differentiation to the megakaryocyte lineage, the following cytokines were used: BMP-4, bFGF and VEGF (all at 10 ng/ml); activin A (0.5-3.0 ng/ml); hSCF (100 ng/ml), hTPO (50 ng/ml), hEPO (2 U/ml), h1L-6 (20 ng/ml), h1L-3 (40 ng/ml), and h1L-11 (5 ng/ml). Using CD41 as an early marker of definitive hematopoiesis and CD42 (GP1b) as a megakaryocyte-specific marker, it was found that day 11 EB generated ~10% $CD41^{Hi}CD42^+$ and ~20% $CD41^{Lo}CD42^±$ populations. Following cell sorting and culture in TPO-containing media, both populations underwent further differentiation as shown by increased CD41 and CD42 expression and by morphology (May-Grunwald-Giemsa staining). Using gene expression profiles, and progenitor and functional assays, it was found that the $CD41^{Hi}CD42^+$ population of cells was committed to the megakaryocyte lineage.

EXAMPLE 4

Infused Megakaryocytes Release Platelets

Infused WT platelets into mice expressing only human CD41 (Thornton et al. (2002) Blood 100:3588-96; Massberg et al. (2005) Circulation 112:1180-8) caused a rise in platelets consistent with the number of transfused platelets and the starting platelet count in the recipient mouse. These platelets had a half-life of ~30 hours. When WT megakaryocytes from cultured fetal livers (after 8 days growth in TPO media (Ikuta et al. (1990) Cell 62:863-74)) were infused, the rise in platelets in the same recipient mice was ~70% of the expected rise if one murine megakaryocyte gives rise to $10^3$ platelets. However, there was a delay in platelet appearance at 5 minutes and the half-life may be shorter than with infused platelets. The delay in platelet count rise is consistent with the megakaryocytes having to release platelets in the lungs. The shorter half-life may be due to a recently described metalloproteinase present in the culture media inhibitable by inclusion of GM6001 (Nishikii et al. (2008) J. Exp. Med., 205:1917-27). Of note, none of the animals developed obvious respiratory or vascular problems with the infused megakaryocytes indicating that infusing megakaryocytes are clinically feasible.

EXAMPLE 5

Expression of Proteins of Interest

Ectopic proteins can be expressed in developing megakaryocytes and stored in platelet α-granules. For example, when FVIII is expressed during megakaryopoiesis, it is stored in circulating platelets with no detectable FVIII in the plasma of $FVIII^{null}$ mice (Gewirtz et al. (2008) J. Thromb. Haemost., 6:1160-6). Platelet-released FVIII (pFVIII) is effective even in the presence of circulating inhibitors. Transfused platelets from mice that express pFVIII can correct the bleeding diathesis in $FVIII^{null}$ mice (Yarovoi et al. (2003) Blood 102: 4006-13; Yarovoi et al. (2005) Blood 105:4674-6).

Similarly, ectopically expressed uPA during megakaryopoiesis is stored in the α-granules of circulating platelets, but did not cause systemic fibrinolysis (Kufrin et al. (2003) Blood 102:926-33) yet markedly enhanced thrombolysis. Transfused platelets containing uPA into WT mice also enhanced fibrinolysis in recipient mice (Karin et al. (2003) Blood 102:926-33).

EXAMPLE 6

Figure 7A:
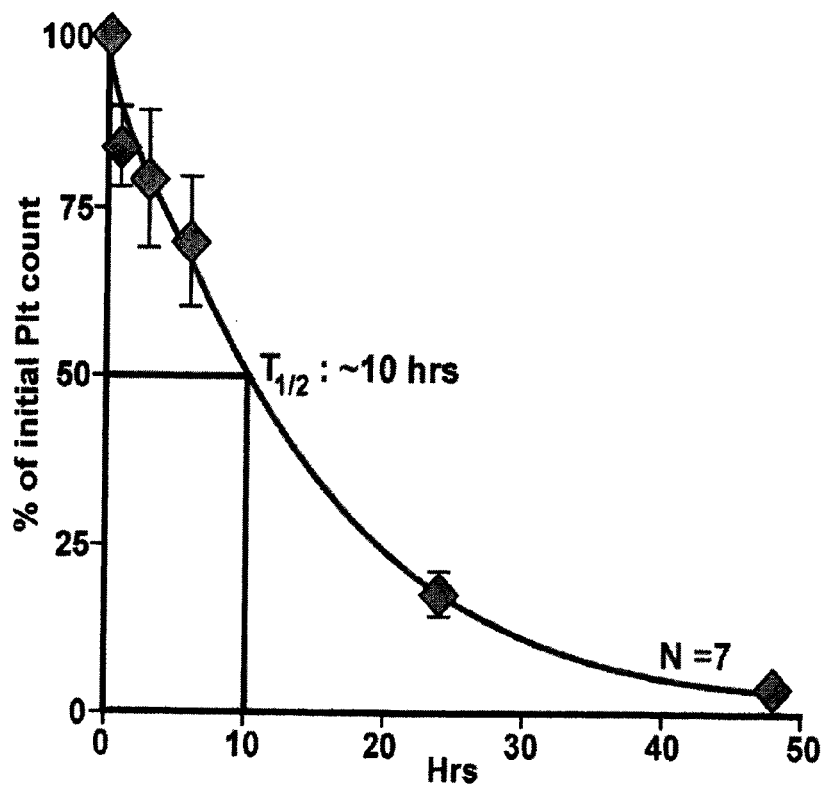
FIG. 7A provides a graph of human platelets infused into immune-suppressed NOD/SCID/interferon-gamma NSG mice over time.
Figure 7B:
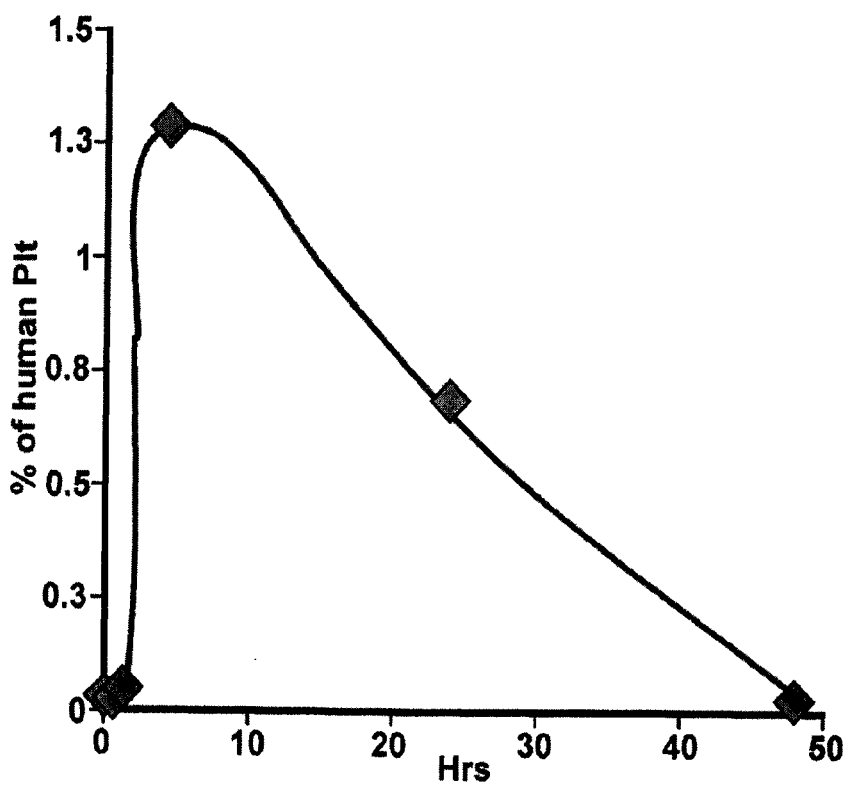
FIG. 7B provides a graph of the percentage of human platelets over time after infusion of fetal liver megakaryocytes into NSG mice.

NSG mice (Shultz et al. (2007) Nat. Rev. Immunol., 7:118-130; Shultz et al. (2005) J. Immunol., 174:6477-89) were infused with human platelets. As seen in FIG. 7A, the half-life of the human platelets was about 10 hours. When human fetal liver (FL) megakaryocytes were infused into NSG mice, a spike of platelets was observed within 10 hours of infusion (FIG. 7B). Two million large cells infused yielded about 13 platelets per megakaryocyte. The human megakaryocytes were also incorporated in growing thrombi.

Figure 7C:
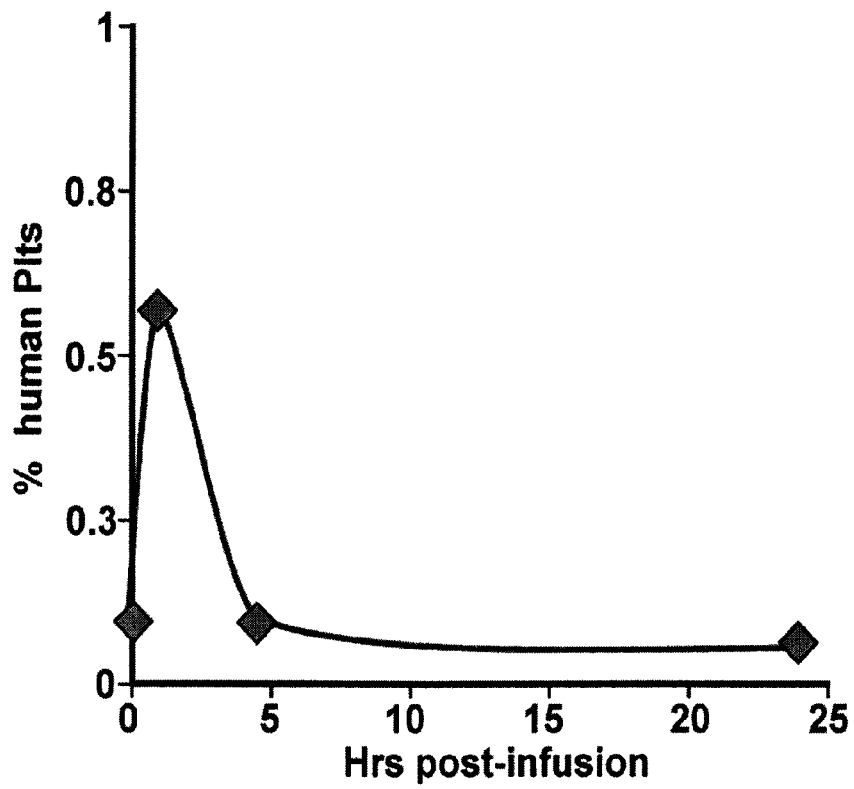
FIG. 7C provides a graph of human platelets over time after infusion of dimethylfasudil (diMF; 5 μM), a Rho/ROCK1 kinase inhibitor, treated human fetal liver megakaryocytes (large cells) into NSG mice.
Figure 7D:
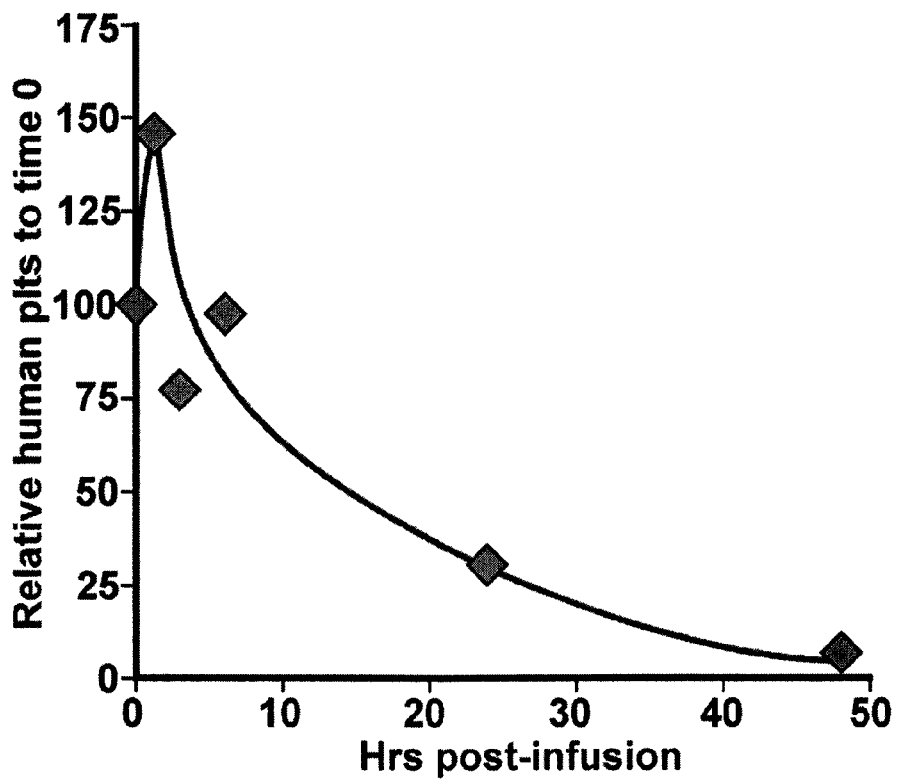
FIG. 7D provides a graph of human platelets over time after infusion of human megakaryocytes (large cell) from CD34+ bone marrow cells into NSG mice.
Figure 7E:
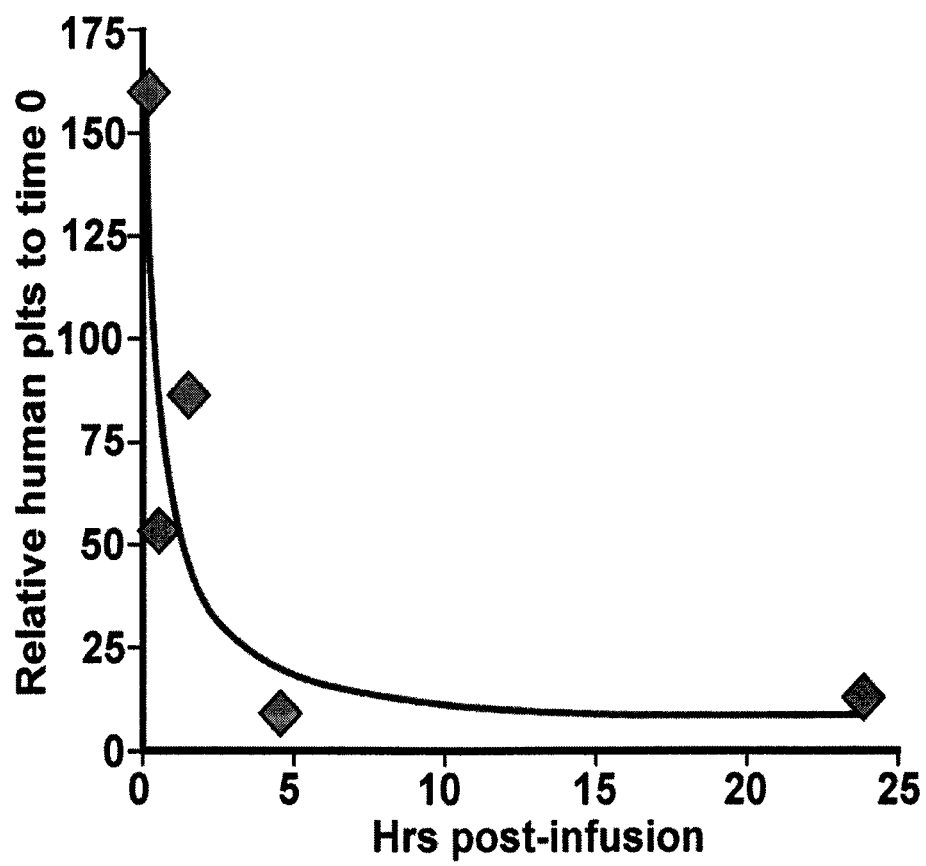
FIG. 7E provides a graph of human platelets over time after infusion of dimethylfasudil (2 µM)-treated human CD34+ bone marrow megakaryocytes (large cell) into NSG mice.

To increase platelet production, dimethylfasudil (diMF), a Rho/ROCK1 kinase inhibitor, was tested for its ability to promote human FL megakaryocyte maturation. When FL-megakaryocytes (large) were treated with DiMF (5 μm) and infused into NSG mice, a spike of platelets was observed within about one hour of infusion (FIG. 7C). Further, the infusion of two million large cells yielded only about 6 platelets per megakaryocyte. Next, human-Megs (large) from bone marrow (BM) CD34+ cells were infused into NSG mice. As seen in FIG. 7D, platelets peaked within a few hours of infusion. Further, the infusion of two million large cells yielded about 70 platelets per megakaryocyte. When BM CD34+ Megs (large) were treated with DiMF (2 μm) and infused into NSG mice, a spike of platelets was observed immediately (FIG. 7E). Further, the infusion of two million large cells yielded only about 4 platelets per megakaryocyte.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of treating thrombocytopenia in a subject, said method comprising:
   a) decreasing the expression of GATA-1 in human pluripotent stem cells, thereby generating GATA-1 knockout or knockdown stem cells;
   b) culturing the GATA-1 knockout or knockdown stem cells in the presence of thrombopoietin, thereby generating a self-replicating, megakaryocyte-erythroid progenitor (MEP)-like cell line (G1ME);
   c) expressing GATA-1 in said G1ME cells, thereby differentiating the cells into terminal erythrocytes and megakaryocytes;
   d) isolating megakaryocytes from the cells of step c); and
   e) administering the isolated megakaryocytes to said subject, thereby treating said thrombocytopenia,
   wherein step a) comprises delivering GATA-1 antisense, GATA-1 siRNA, GATA-1 shRNA, or a nucleic acid molecule encoding said antisense, siRNA or shRNA to the human pluripotent stem cells.

2. The method of claim 1, wherein said human pluripotent stem cells are human embryonic stem cells or induced pluripotent stem (iPS) cells.

3. The method of claim 1, further comprising the delivery of a nucleic acid molecule encoding a protein of interest to the cells prior to step e).

4. The method of claim 3, further comprising the delivery of a nucleic acid molecule encoding a protein of interest to said G1ME cells.

5. The method of claim 1, wherein step c) comprises removal of the suppression of GATA-1 expression by said GATA-1 antisense, GATA-1 siRNA, GATA-1 shRNA, or by the nucleic acid molecule encoding said antisense, siRNA or shRNA.

6. The method of claim 1, wherein step c) comprises expressing GATA-1 to native levels.

7. The method of claim 1, wherein step b) further comprises culturing the GATA-1 knockout or knockdown stem cells with stromal cells.

8. The method of claim 1, wherein step d) comprises isolating cells having a diameter of at least about 50 μm.

9. The method of claim 3, wherein said protein of interest is a procoagulant protein.

* * * * *